(12) United States Patent
Ried et al.

(10) Patent No.: US 8,409,808 B2
(45) Date of Patent: Apr. 2, 2013

(54) METHOD FOR DETECTING RISK OF PROGRESSION OF LOW GRADE CERVICAL DYSPLASIA

(75) Inventors: Thomas Ried, Bethesda, MD (US); Kerstin Heselmeyer-Haddad, Rockville, MD (US); Winfried Steinberg, Soest (DE); Gert Auer, Stockholm-Solna (SE); Sonia Andersson, Stockholm (SE); Catharina Larsson, Stockholm (SE)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 1043 days.

(21) Appl. No.: 11/884,608

(22) PCT Filed: Feb. 21, 2006

(86) PCT No.: PCT/US2006/006116
§ 371 (c)(1),
(2), (4) Date: Sep. 8, 2008

(87) PCT Pub. No.: WO2006/089287
PCT Pub. Date: Aug. 24, 2006

(65) Prior Publication Data
US 2009/0035763 A1    Feb. 5, 2009

Related U.S. Application Data

(60) Provisional application No. 60/654,176, filed on Feb. 18, 2005.

(51) Int. Cl.
*C12Q 1/68* (2006.01)
*G01N 33/53* (2006.01)
*C07H 21/04* (2006.01)
*C12N 9/10* (2006.01)

(52) U.S. Cl. .............. 435/6.14; 435/6.11; 435/6.12; 435/7.1; 435/193; 536/23.2

(58) Field of Classification Search .................. None
See application file for complete search history.

(56) References Cited

U.S. PATENT DOCUMENTS 5,919,624 A      7/1999   Ried et al.
2004/0248107 A1  12/2004  Sokolova et al.
2005/0026190 A1  2/2005   Sokolova et al.

OTHER PUBLICATIONS

K. Umayahara et al., "Comparative Genomic Hybridization Detects Genetic Alterations During Early Stages of Cervical Cancer Progression", Gene, Chromosomes & Cancer, vol. 33, pp. 98-102 (2002).
Heselmeyer-Haddad Kerstin et al., American Journal of Pathology, 163(4):1405-1416 (2003).
Heselmeyer-Haddad Kerstin et al., American Journal of Pathology, 166(4):1229-1238 (2005).

*Primary Examiner* — Diana Johannsen
(74) *Attorney, Agent, or Firm* — Edwards Wildman Palmer LLP; Peter F. Corless

(57) ABSTRACT

The invention provides methods for identifying conditions of low grade cervical dysplasia and assessing the progressive potential of individual lesions to develop into high grade cervical dysplasia and cervical squamous cell cancer as well as cervical adenocarcinoma.

14 Claims, 4 Drawing Sheets

METHOD FOR DETECTING RISK OF PROGRESSION OF LOW GRADE CERVICAL DYSPLASIA

STATEMENT OF RIGHTS TO INVENTION MADE UNDER FEDERALLY SPONSORED RESEARCH

This work was supported by the National Institutes of Health. The government may have certain rights to this invention.

RELATED APPLICATIONS/PATENTS & INCORPORATION BY REFERENCE

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

BACKGROUND OF THE INVENTION

The visualization of chromosomal aneuploidy and copy number changes of specific cancer-associated genes has become an important complement to routine morphological assessment of cytological samples.[1] This approach is biologically valid and successful because chromosomal aneuploidy and the resulting genomic imbalances are specific for cancer cells, distinct for different carcinomas, and occur early during disease progression.[2,3] Some genomic imbalances are correlated with poor prognosis and treatment failure,[4-6] and others, such as amplification of the Her2/neu oncogene in breast cancer, can guide therapeutic decisions.[7]

Like most other human carcinomas, cervical cancers are defined by a conserved distribution of genomic imbalances. In addition to infection with high-risk human papilloma virus,[9,10] the sequential transformation of cervical squamous epithelium requires the acquisition of additional copies of chromosome arm 3q,[11] among other cytogenetic abnormalities.[12] CGH analyses of cervical carcinomas have shown that more than 85% of invasive cervical carcinomas carry specific genomic imbalances that result in copy number increases of chromosome arm 3q.[5,11,20-26] The region of minimal overlap points to chromosome band 3q26, which contains the gene for the RNA component of human telomerase (TERC).[27]

The implementation of cervical cancer screening programs has greatly reduced disease incidence and mortality in industrialized countries.[16,17] However, a single cytological evaluation remains relatively insensitive, hence the need for frequent follow-up investigations. This is attributable to sampling or interpretation errors, and to the fact that some early lesions may not have acquired recognizable phenotypic alterations.[17] Invasive cervical carcinomas develop through increasing stages of cervical dysplasia and advance to CIN3, which is considered a bonafide precancerous lesion that requires surgical intervention. However, only about 10-15% of all low-grade dysplastic lesions follow this path of linear progression. The identification of markers of disease progression would therefore be of great clinical interest.

A previous study demonstrated that visualization of additional copies of TERC can serve as a specific and sensitive test for 3q26 amplification in routinely collected cytological samples, including samples of low grade cervical dysplasia.[8] This finding was consistent with, but not conclusive of, the hypothesis that the 3q-imposed growth advantage reflects a point of no return during the sequential malignant transformation of cervical epithelial cells. For example, U.S. application Ser. No. 10/857,859, filed on Jun. 4, 2004 and published as U.S. Application Publication No. 20050026190, indicates that the 3q26 amplification can be used to selectively detect high grade cervical intraepithelial neoplasias (CIN II and CIN III) and malignant carcinomas in cervical biopsy and pap smear specimens without detecting low grade cervical intraepithelial neoplasia. Thus, the 3q26 amplification was thought to be a distinguishing factor between low grade and high grade cervical dysplasias and adenocarcinomas.

SUMMARY OF THE INVENTION

It has now been that demonstrated that identification of a 3q amplification in low grade cervical dysplasia can provide information regarding the progressive potential of individual lesions to high grade cervical dysplasia and cancer.

In one aspect, the present invention provides a method for assessing a change in a patient condition of low grade cervical dysplasia to a condition of high grade cervical dysplasia or cancer, comprising: detecting a genomic amplification of chromosome 3q in a sample from a patient having or previously having low grade cervical dysplasia to thereby assess the change in the patient condition to a high grade cervical dysplasia or cancer. Detecting the genomic amplification of chromosome 3q indicates progression of the patient condition to high grade cervical dysplasia.

In another aspect, the present invention provides a method for monitoring a shift to a condition of high grade cervical dysplasia from a condition of low grade cervical dysplasia in a patient comprising: assaying for a genomic amplification of chromosome 3q in a sample from a patient having or previously having low grade cervical dysplasia to thereby monitor a shift to a condition of high grade cervical dysplasia from a condition of low grade cervical dysplasia. The method can further comprising determining that the genomic amplification of chromosome 3q is present in the sample or that the genomic amplification of chromosome 3q is not present in the sample.

Low grade cervical dysplasias of the invention can be but are not limited to cervical intraepithelial neoplasms of grade 1. High grade cervical dysplasias of the invention include but are not limited to cervical intraepithelial neoplasms of grade 2, cervical intraepithelial neoplasms of grade 3 and carcinomas in situ.

In one embodiment, the sample obtained from the patient is a preparation from the cervix, including but not limited to a pap smear or a thin layer (e.g., mono-layer) suspension of cells.

According to specific embodiments of the invention, the genomic amplification can be within the 3q26 locus of chromosome 3q. This locus includes the coding sequences of the telomerase (TERC) gene. Thus, in one embodiment, the genomic amplification is detected by hybridizing the sample to a probe comprising a detectable marker and a nucleic acid sequence that is complimentary to a nucleic acid sequence of the 3q26 locus. Methods of the invention can further involve hybridizing the sample to a centromere enumeration probe comprising a detectable marker and a nucleic acid sequence that is complimentary to a nucleic acid sequence proximate to the centromere of chromosome 3.

In one embodiment, the nucleic acid sequence of the probe is complimentary to the telomerase gene, or a portion thereof.

In other embodiments, the nucleic acid sequence of the probe is complimentary to a nucleic acid sequence of chromosome 3q, or a portion thereof, including but not limited to EVI1 (ectopic viral integration site 1, 3q24-3q28), MDS1 (myelodysplasia syndrome 1, 3q26), MYNN (myoneurin, 3q26.2), GPR160 (G protein-coupled receptor 160, 3q26.2-3q27), PRKCI (protein kinase C, 3q26.3), SKIL (SKI-like 3q26), CLDN11 (claudin 11, 3q26.2-3q26.3), EIF5A2 (eukaryotic translation initiation factor 5A2, 3q26.2), TNIK (TRAF2 and NCK interacting kinase, 3q26.2), PLD1 (phospholipase D1, 3q26), GHSR (growth hormone secretagogue receptor, 3q26.31), TNSF10 (tumor necrosis factor 10, 3q26), ECT2 (epithelial cell transforming sequence 2 oncogene, 3q26.1-3q26.2), WIG1 (p53 target zinc finger protein, 3q26.3-3q27), PIK3A (phosphoinositide-3-kinase, 3q26.3), MFN1 (mitofusin 1, 3q26.32) and USP13 (ubiquitin specific protease 13, 3q26.2-3q26.3).

In another embodiment, the detectable marker of the probe emits a fluorescent signal.

In yet another embodiment, the detectable marker of the probe is chromogenic.

In yet another embodiment, the genomic amplification is detected by Polymerase Chain Reaction (PCR).

In yet another embodiment, the genomic amplification is detected by measuring the amount of a polypeptide transcribed from a gene having a locus within the genomic amplification.

In a specific embodiment, the genomic amplification is detected by measuring the amount of the telomerase polypeptide.

In yet another aspect, the present invention provides a method for identifying a patient at risk of developing invasive cervical carcinoma, comprising: making a first identification of a genomic amplification of chromosome 3q in a sample obtained from a patient known to have had a condition of either i) low grade cervical dysplasia or ii) no dysplasia thereby identifying a patient at risk of developing invasive cervical carcinoma.

In a specific embodiment, a cytologically normal pap smear can be obtained from a patient having no dysplasia but having a genomic amplification of chromosome 3q.

In yet another aspect, the present invention provides a method for assessing maintenance or regression of a patient condition of low grade cervical dysplasia comprising: a) assaying for a genomic amplification of chromosome 3q in a sample from a patient having or previously having low grade cervical dysplasia and b) determining that the genomic amplification of step a) is not present, wherein the absence of the genomic amplification of step a) indicates maintenance or regression of the patient condition of low grade cervical dysplasia.

In one embodiment, regression is detected by obtaining a cytologically normal pap smear from the patient.

In other aspects of the invention, kits are provided for conducting methods of the invention.

In one embodiment, the present invention provides a kit for assessing a change in a patient condition of low grade cervical dysplasia to a condition of high grade cervical dysplasia comprising a probe for detecting a genomic amplification of chromosome 3q and instructions for using the probe to assess the change in a patient condition of low grade cervical dysplasia to a condition of high grade cervical dysplasia in accordance with methods of the invention.

In another embodiment, the present invention provides a kit for identifying a patient at risk of developing invasive cervical carcinoma comprising a probe for detecting a genomic amplification of chromosome 3q and instructions for using the probe to identify a patient at risk of developing invasive cervical carcinoma in accordance with methods of the invention.

In yet another embodiment, the present invention provides a kit for monitoring a shift to a condition of high grade cervical dysplasia from a condition of low grade cervical dysplasia in a patient comprising a probe for detecting a genomic amplification of chromosome 3q and instructions for using the probe to monitor the shift to a condition of high grade cervical dysplasia from a condition of low grade cervical dysplasia in accordance with methods of the invention.

In yet another embodiment, the present invention provides a kit for assessing maintenance or regression of a patient condition of low grade cervical dysplasia comprising a probe for detecting a genomic amplification of chromosome 3q and instructions for using the probe to assess maintenance or regression of a patient condition of low grade cervical dysplasia in accordance with methods of the invention.

In one aspect, methods for assessing a change in a patient condition of normal to a condition of low grade cervical dysplasia, high grade cervical dysplasia or cancer and provided and comprise detecting a genomic amplification of chromosome 3q in a sample from a patient having or previously having a normal diagnosis to thereby assess the change in the patient condition to a low grade cervical dysplasia, high grade cervical dysplasia or cancer.

In one embodiment, detecting the genomic amplification of chromosome 3q indicates progression of the patient condition to low grad or high grade cervical dysplasia.

In another embodiment, the genomic amplification is within the 3q26 locus of chromosome 3q.

In one aspect, methods of diagnosing adenocarcinoma in a subject are provided and comprise detecting genomic amplification of a telomerase gene or portion thereof in a subject.

In one embodiment, the genomic amplification is detected by hybridizing the sample to a probe comprising a detectable marker and a nucleic acid sequence that is complimentary to a nucleic acid sequence of the 3q26 locus.

In another embodiment, the probe comprises a contig of four overlapping BAC clones. In related embodiments, the probe comprises five or six overlapping BAC clones.

In yet another embodiment, the nucleic acid sequence of the probe is complimentary to the telomerase gene, or a portion thereof.

In certain embodiments, the sample is a preparation from the cervix.

In one embodiment the methods may further comprise hybridizing the sample to a centromere enumeration probe comprising a detectable marker and a nucleic acid sequence that is complimentary to a nucleic acid sequence proximate to the centromere of chromosome 3.

In one embodiment the methods may further comprise hybridizing the sample to a centromere enumeration probe comprising a detectable marker and a nucleic acid sequence that is complimentary to a nucleic acid sequence proximate to the centromere of chromosome 7.

In one embodiment the methods may further comprise hybridizing the sample to a centromere enumeration probe comprising a detectable marker and a nucleic acid sequence that is complimentary to a nucleic acid sequence proximate to the centromere of chromosomes 3 and 7.

In one aspect, kits for monitoring an adenocarcinoma in a patient are provided and comprise a probe for detecting a genomic amplification of chromosome 3q and instructions for using the probe to monitor adenocarcinoma in accordance with the methods described herein.

Other aspects of the invention are described in or are obvious from the following disclosure, and are within the ambit of the invention.

BRIEF DESCRIPTION OF THE DRAWINGS

The following Detailed Description, given by way of example, but not intended to limit the invention to specific embodiments described, may be understood in conjunction with the accompanying drawings, incorporated herein by reference. Various preferred features and embodiments of the present invention will now be described by way of non-limiting example and with reference to the accompanying drawings in which.

DETAILED DESCRIPTION OF THE INVENTION

I. Definitions

Figure 1:
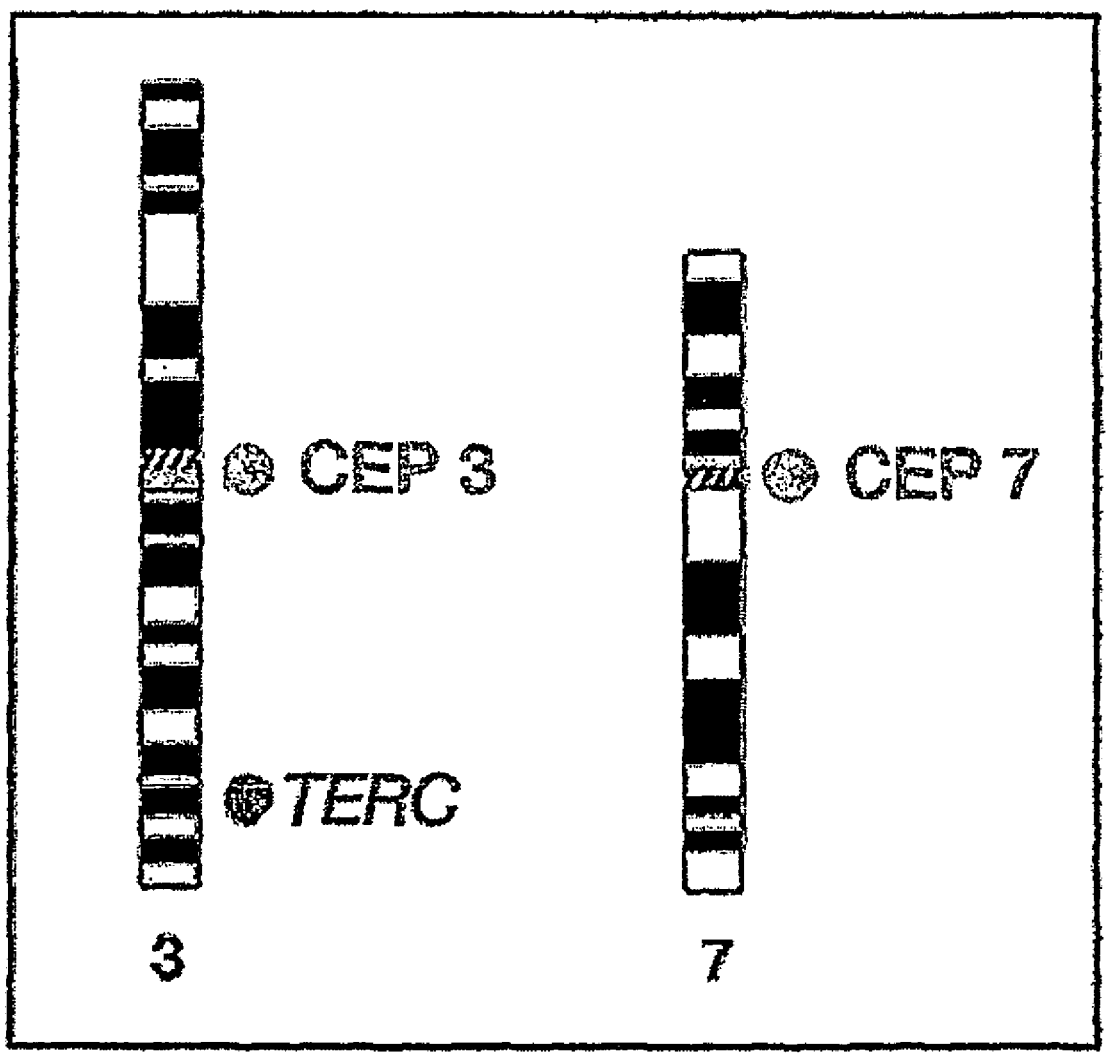
FIG. 1 schematically depicts the triple-color FISH probe set (Heselmeyer-Haddad et al., 2003).

"Adenocarcinoma" refers at least to a cervical carcinoma as known to one of skill in the art. Cervical adenocarcinoma develops at least in part from the mucus-producing gland cells of the endocervix.

"Low grade cervical dysplasia" refers to minor dysplastic cervical lesions including cervical intraepithelial neoplasms of grade 1.

"High grade cervical dysplasia" refers to carcinoma in situ or high-grade squamous intraepithelial lesions including cervical intraepithelial neoplasms of grade 2 or 3.

"Cervical intraepithelial neoplasms" or "CINs" are categorized as grade 1, 2, or 3 depending on the extent of aberration in cellular stratification. CIN 1 is characterized by the presence of immature basal type cells in the lower third of the epithelium. CIN 2 is characterized by the presence of immature basal type cells in the lower two-thirds of the epithelium. In CIN 3, the full thickness of the epithelium contains undifferentiated and nonstratified cells.

"Progression" of a patient condition of low grade cervical dysplasia refers to malignant conversion of minor cervical dysplastic lesions such as cervical intraepithelial neoplasms of grade 1 or grade 2 to high grade cervical dysplasias.

"Maintenance" of a patient condition of low grade cervical dysplasia refers to the continued presence of minor dysplastic cervical lesions over time.

"Regression" of a patient condition of low grade cervical dysplasia refers to a reduction or eradication of minor dysplastic lesions over time. Eradication can be detected by a cytologically normal pap smear in a patient previously diagnosed with low grade cervical dysplasia.

"Genomic amplification" refers to a copy number increase in a genomic sequence, such as a sequence encoding one or more genes.

A "locus" refers to a chromosomal region defined according to genetic maps of an organism. Typically, the genetic maps designate the specific position (i.e., the "locus") occupied by a given gene on a chromosome and at a particular locus, any one of the variant genes may be present.

A "nucleic acid sequence" refers to a deoxyribonucleotide or ribonucleotide polymer in either single- or double-stranded form, and unless otherwise stated, would encompass known analogs of natural nucleotides that can function in a similar manner as naturally occurring nucleotides.

"Complimentary nucleic acid sequences" refer to contiguous DNA or RNA sequences which have compatible nucleotides (e.g., A/T, G/C) in corresponding positions, such that base pairing between the sequences occurs. For example, the sense and anti-sense strands of a double-stranded DNA helix are known in the art to be complimentary.

A "probe" or a "nucleic acid probe", as used herein, is defined to be a collection of one or more nucleic acid fragments whose hybridization to a chromosomal nucleic acid sequence can be detected.

"Hybridizing" refers to the binding of two single stranded nucleic acids via complementary base pairing as well as to two or more nucleic acids.

A "centromere enumeration probe" is a probe that hybridizes to a chromosomal region proximate to the centromere, usually a repeat sequence region, and can indicate the presence or absence of an entire chromosome.

A "patient" is a female subject, preferably human, having or previously having cancer or cervical dysplasia, e.g., low grade cervical dysplasia, or a cytologically normal pap smear Other definitions appear in context throughout the disclosure.

II. Methods of the Invention

Preparation of Samples

Biological samples obtained from patients are typically cervical preparations, including a pap smear or a thin layer suspension of cells. A biological sample is a sample that contains cells or cellular material, e.g., cells or material derived from the uterine cervix of the uterus. Examples of cervical specimens include cervical biopsies, smears, scrapes and the like. Typically, cells are harvested from a biological sample and prepared using techniques well known in the art. Samples can comprise any number of cells that is sufficient for a clinical diagnosis, and typically contain at least about 100 cells. In a typical assay, the hybridization pattern is assessed in about 25-5,000 cells. Numerous methods are available for collecting cervical cells for evaluation. For example, cells from the ectocervix and endocervix/transformation zone are collected using well-known devices such as endocervical brushes (or "brooms") or wooden and plastic spatulas. Conventional smears are prepared by spreading cells evenly and thinly onto a glass slide. The slide is then fixed rapidly by immersion into 95% ethanol or spraying with a commercial fixative according to manufacturer instructions.

For the ThinPrep™ collection method (Cytyc Corp., Boxborough, Mass.), cells are transferred from the cervix into the fixative PreservCyt™. This allows cells to be preserved until ready for further processing. Cells are then gently dispersed, randomized and collected onto a TransCyt™ membrane filter by drawing the sample across the filter with a vacuum until an optimal number of cells is deposited into the filter. The cells can be further processed as desirable. In another method, the cells collected into PreservCyt™ or other fixative solution can be further washed by centrifuging, removing the supernatant and resuspending in Carnoys solution (3:1 Methanol: Acetic acid), repeating (e.g., three times) as desired. Cells are then transferred to a glass slide by dropping a small aliquot of cell suspension directly onto the slide. Slides are typically dried overnight.

Where hybridization methods are desired, such biological samples comprise DNA in a form suitable for hybridization to one of the probes of the invention. The nucleic acid can be total genomic DNA, total mRNA, genomic DNA or mRNA from particular chromosomes, or selected sequences (e.g. 3q sequences).

The biological sample can optionally be prepared such that the nuclei in the biological sample remain substantially intact and comprise interphase nuclei prepared according to standard techniques. The biological sample can also comprise substantially intact condensed chromosome (e.g. a metaphase chromosome). Such condensed chromosomes or interphase nuclei are suitable for use as hybridization targets in situ hybridization techniques (e.g. FISH).

Detection of Chromosomal Abnormalities

An overabundance of mRNA and protein can result from transcription of duplicated genes within the amplified region of chromosome 3q. Accordingly, methods for detecting the genomic amplification can include methods known in the art for measuring mRNA levels (e.g., RT-PCR) and protein levels (e.g., western blotting, enzyme linked immunosorbent assays (ELISAs), immunoprecipitations and immunofluorescence). Protein expression can be evaluated using an immunoassay. An immunoassay is an assay that utilizes an antibody to specifically bind to the analyte (e.g., telomerase protein). The immunoassay is characterized by detection of specific binding of the protein to an antibody. Western blot (immunoblot) analysis can also be used to quantify the presence of the proteins in the sample. This technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the desired protein.

Genomic amplifications can also be identified through hybridization methods in which a probe is bound to a nucleotide sequence within a sample or obtained from a sample. Essentially, the genomic amplification is detected by hybridizing a probe that is complimentary to a nucleic acid sequence of chromosome 3q (e.g., 3q26).

Suitable hybridization formats are well known to those of skill in the art and include, but are not limited to, variations of southern blots, northern blots, CGH, in situ hybridization and quantitative amplification methods such as quantitative PCR (see, e.g. Sambrook et al., Kallioniemi et al., Proc. Natl. Acad Sci USA, 89: 5321-5325 (1992), and PCR Protocols, A Guide to Methods and Applications, Innis et al., Academic Press, Inc. N.Y., (1990)). The sample can also comprise isolated nucleic acids immobilized on a solid surface (e.g., nitrocellulose) for use in southern or dot blot hybridizations and the like. In various blot formats (e.g., dot blots, Southern blots, and Northern blots) nucleic acids (e.g., genomic DNA, cDNA or RNA) are hybridized to a probe specific for the target region. Either the probe or the target can be immobilized on the solid surface. Procedures for carrying out Southern hybridizations are well known to those of skill in the art. see, e.g., Sambrook et al.

Gain or loss of chromosomes or chromosomal regions can be assessed by methods of in situ hybridization in which the hybridization pattern of the chromosomal probe or set of chromosomal probes (e.g., the number of signals for each probe) is examined, and the number of signals is recorded. In situ hybridization comprises the following major steps: (1) fixation of tissue or biological structure to analyzed; (2) prehybridization treatment of the biological structure to increase accessibility of target DNA, and to reduce nonspecific binding; (3) hybridization of the mixture of nucleic acids to the nucleic acid in the biological structure or tissue; (4) posthybridization washes to remove nucleic acid fragments not bound in the hybridization and (5) detection of the hybridized nucleic acid fragments. The reagent used in each of these steps and their conditions for use vary depending on the particular application.

In some applications it is necessary to block the hybridization capacity of repetitive sequences. In this case, human genomic DNA or Cot1 DNA is used as an agent to block such hybridization. The preferred size range is from about 200 bp to about 1000 bases, more preferably between about 400 to about 800 bp for double stranded, nick translated nucleic acids.

Hybridization protocols for the particular applications disclosed here are described in Pinkel et al. Proc. Natl. Acad. Sci. USA, 85: 9138-9142 (1988) and in EPO Pub. No. 430,402. Suitable hybridization protocols can also be found in Methods in Molecular Biology Vol. 33: In Situ Hybridization Protocols, K. H. A. Choo, ed., Humana Press, Totowa, N.J., (1994) and Kallioniemi et al., Proc. Natl. Acad Sci USA, 89: 5321-5325 (1992).

Typically, it is desirable to use dual color FISH, in which two probes are utilized, each labeled by a different fluorescent dye. A test probe that hybridizes to the region of interest is labeled with one dye, and a control probe that hybridizes to a different region is labeled with a second dye (e.g., a centromere enumeration probe). A nucleic acid that hybridizes to a stable portion of the chromosome of interest, such as the centromere region, is often most useful as the control probe. In this way, differences between efficiency of hybridization from sample to sample can be accounted for.

The FISH methods for detecting chromosomal abnormalities can be performed on single cells from the sample. Paraffin embedded tumor sections can be used, as can fresh or frozen material. Because FISH can be applied to the limited material, touch preparations prepared from uncultured primary tumors can also be used (see, e.g., Kallioniemi, A. et al., Cytogenet. Cell Genet. 60: 190-193 (1992)). For instance, small biopsy tissue samples from tumors can be used for touch preparations (see, e.g., Kallioniemi, A. et al., Cytogenet. Cell Genet. 60: 190-193 (1992)). Small numbers of cells obtained from aspiration biopsy or cells in bodily fluids (e.g., blood, urine, sputum and the like) can also be analyzed. Comparison of the intensity of the hybridization signal from the probe for the target region with the signal from a probe directed to a control (non amplified or deleted) such as centromeric DNA, provides an estimate of the relative copy number of the target nucleic acid.

Chromosomal Probes

Using the results provided here, one of skill can prepare nucleic acid probes that are complimentary to the sequences of 3q known to have genetic alterations. In particular, such nucleic acid sequences include but are not limited to TERC (telomerase, 3q26), EVI1 (ectopic viral integration site 1, 3q24-3q28), MDS1 (myelodysplasia syndrome 1, 3q26), MYNN (myoneurin, 3q26.2), GPR160 (G protein-coupled receptor 160, 3q26.2-3q27), PRKCI (protein kinase C, 3q26.3), SKIL (SKI-like 3q26), CLDN11 (claudin 11, 3q26.2-3q26.3), EIF5A2 (eukaryotic translation initiation factor 5A2, 3q26.2), TNIK (TRAF2 and NCK interacting kinase, 3q26.2), PLD1 (phospholipase D1, 3q26), GHSR (growth hormone secretagogue receptor, 3q26.31), TNSF10 (tumor necrosis factor 10, 3q26), ECT2 (epithelial cell transforming sequence 2 oncogene, 3q26.1-3q26.2), WIG1 (p53 target zinc finger protein, 3q26.3-3q27), PIK3A (phosphoinositide-3-kinase, 3q26.3), MFN1 (mitofusin 1, 3q26.32) and USP13 (ubiquitin specific protease 13, 3q26.2-3q26.3).

In a preferred embodiment, a genomic probe for the telomerase (TERC) gene on chromosome band 3q26 is applied in combination with two control probes (CEP3 and CEP7).

The probe is often labeled with a detectable marker so that its binding to the target nucleic acid sequence can be identified. In some embodiments the probes are attached to a solid surface as an array of nucleic acid molecules. The probe is produced from a source of nucleic acids from one or more particular (preselected) portions of the genome, for example one or more clones, an isolated whole chromosome or chromosome fragment, or a collection of polymerase chain reaction (PCR) amplification products. The probes of the present invention are produced from nucleic acids found in the regions of genetic alteration as described herein. The probe can be processed in some manner, for example, by blocking or removal of repetitive nucleic acids or enrichment with unique nucleic acids.

The sample or the probes used in the invention can be isolated nucleic acids immobilized on a solid surface (e.g., nitrocellulose) for use in Southern or dot blot hybridizations and the like. In some embodiments, the sample or probes may comprise an array of nucleic acids as described for instance in WO 96/17958. The techniques capable of producing high density arrays for various applications are also known in the art (see, e.g., Fodor et al. Science 767-773 (1991) and U.S. Pat. No. 5,143,854). In some cases, the nucleic acids can be amplified using standard techniques such as PCR, prior to the hybridization.

A number of methods can be used to identify probes which hybridize specifically to the 3q26 region other than those exemplified here. For instance, probes can be generated by the random selection of clones from a chromosome specific library, and then mapped by digital imaging microscopy. This procedure is described in U.S. Pat. No. 5,472,842. Briefly, a genomic or chromosome specific DNA is digested with restriction enzymes or mechanically sheared to give DNA sequences of at least about 20 kb and more preferably about 40 kb to 300 kb. Techniques of partial sequence digestion are well known in the art. See, for example Perbal, A Practical Guide to Molecular Cloning 2nd Ed., Wiley N.Y. (1988). The resulting sequences are ligated with a vector and introduced into the appropriate host. Exemplary vectors suitable for this purpose include cosinids, yeast artificial chromosomes (YACs), bacterial artificial chromosomes (BACs) and P1 phage. Various libraries spanning entire chromosomes are also available commercially from for instance Genome Systems. Alternatively, libraries can be obtained from the BAC/PAC clone registry or from for the Caltech clones.

Once a probe library is constructed, a subset of the probes is physically mapped on chromosome 3q. FISH and digital image analysis can be used to localize clones along the desired chromosome. Briefly, the clones are mapped by FISH to metaphase spreads from normal cells using e.g., FITC as the fluorophore. The chromosomes can be counterstained by a stain which stains DNA irrespective of base composition (e.g., propidium iodide), to define the outlining of the chromosome. The stained metaphases are imaged in a fluorescence microscope with a polychromatic beam-splitter to avoid color-dependent image shifts. The different color images are acquired with a CCD camera and the digitized images are stored in a computer. A computer program is then used to calculate the chromosome axis, project the two (for single copy sequences) FITC signals perpendicularly onto this axis, and calculate the average fractional length from a defined position, typically the p-telomere. This approach is described, for instance, in U.S. Pat. No. 5,472,842.

Probes that hybridize specific chromosomal loci are available commercially from Vysis, Inc. (Downers Grove, Ill.) and Cancer Genetics, Inc., River Vale, N.J. Alternatively, probes can be made non-commercially using well known techniques. Sources of DNA for use in constructing DNA probes include genomic DNA, cloned DNA sequences such as bacterial artificial chromosomes (BAC), somatic cell hybrids that contain one or a part of a human chromosome along with the normal chromosome complement of the host, and chromosomes purified by flow cytometry or microdissection. The region of interest can be isolated through cloning or by site-specific amplification via the polymerase chain reaction (PCR). See, for example, Nath, et al., Biotechnic Histochem, 1998, 73 (1): 6-22; Wheeless, et al., Cytometry, 1994, 17:319-327; and U.S. Pat. No. 5,491,224. Synthesized oligomeric DNA or PNA probes can also be used.

Sequence information of the genes identified herein permits the design of highly specific hybridization probes or amplification primers suitable for detection of target sequences from these genes. As noted above, the complete sequence of these genes are known. Means for detecting specific DNA sequences within genes are well known to those of skill in the art. For instance, oligonucleotide probes chosen to be complementary to a selected subsequence within the gene can be used. Alternatively, sequences or subsequences may be amplified by a variety of DNA amplification techniques (for example via polymerase chain reaction, ligase chain reaction, transcription amplification, etc.) prior to detection using a probe. Amplification of DNA increases sensitivity of the assay by providing more copies of possible target subsequences. In addition, by using labeled primers in the amplification process, the DNA sequences may be labeled as they are amplified.

The size of the chromosomal region detected by the probes used in the invention can vary, for example, from a several hundred base pair probe sequence to a large segment of 150,000 bases. For locus-specific probes, that are directly labeled, it is preferred to use probes of at least 100,000 bases in complexity, and to use unlabeled blocking nucleic acid, as disclosed in U.S. Pat. No. 5,756,696, herein incorporated by reference, to avoid non-specific binding of the probe. It is also possible to use unlabeled, synthesized oligomeric nucleic acid or protein nucleic acid as the blocking nucleic acid. For targeting a particular gene locus, it is preferred that the probes span the entire genomic coding locus of the gene.

Probe of the invention can be labeled with a detectable marker. Methods of labeling nucleic acids are well known to those of skill in the art. Preferred labels are those that are suitable for use in in situ hybridization. The nucleic acid probes can be detectably labeled prior to the hybridization reaction. Alternatively, a detectable label which binds to the hybridization product may be used. Such detectable labels include any material having a detectable physical or chemical property and have been well-developed in the field of immunoassays.

The labels can be coupled to the probes in a variety of means known to those of skill in the art. In some embodiments the nucleic acid probes are labeled using nick translation or random primer extension (Rigby, et al. J. Mol. Biol., 113: 237 (1977) or Sambrook et al., Molecular Cloning—A Laboratory Manual, Cold Spring Harbor Laboratory, Cold Spring Harbor, N.Y., (1989)). Particularly preferred methods for labeling probes are described in U.S. Pat. No. 5,491,224. These methods involve direct labeling the probes by chemical modification of cytosine residues.

As used herein, a detectable marker is any composition detectable by spectroscopic, photochemical, biochemical, enzymatic, immunochemical, or chemical means. Useful labels in the present invention include radioactive labels (e.g. $^{32}P$, $^{125}I$, $^{14}C$, $^{3}H$, and $^{35}S$), fluorophores (e.g. fluorescein, rhodamine, Texas Red), electron-dense reagents (e.g. gold), enzymes (e.g. enzymes that metabolize substrates to produce a chromogenic signal), colorimetric labels (e.g. colloidal gold), magnetic labels (e.g. Dynabeads™) and the like. Examples of labels which are not directly detected but are detected through the use of directly detectable label include biotin and dioxigenin as well as haptens and proteins for which labeled antisera or monoclonal antibodies are available.

Chromosomal probes can contain any detectable marker that facilitates the detection of the probe when hybridized to a chromosome. Effective markers include both direct and indirect labels as described below.

Chromosomal probes can be directly labeled with a detectable marker. Examples of detectable markers include fluorophores, i.e., organic molecules that fluoresce after absorbing light, and radioactive isotopes, e.g., (e.g. $^{32}P$, $^{125}I$, $^{14}C$, $^{3}H$, and $^{35}S$). Fluorophores can be directly labeled following covalent attachment to a nucleotide by incorporating the labeled nucleotide into the probe with standard techniques such as nick translation, random priming, and PCR labeling. Alternatively, deoxycytidine nucleotides within the probe can be transaminated with a linker. The fluoropore can then be covalently attached to the transaminated deoxycytidine nucleotides. See, e.g., U.S. Pat. No. 5,491,224 to Bittner, et al., which is incorporated herein by reference. Useful probe labeling techniques are described in Molecular Cytogenetics Protocols and Applications, Y.-S. Fan, Ed., Chap. 2, "Labeling Fluorescence In Situ Hybridization Probes for Genomic Targets", L. Morrison et. al., p. 21-40, Humana Press, (2002), incorporated herein by reference.

Examples of fluorophores that can be used in the methods described herein are: 7-amino-4-methylcoumarin-3-acetic acid (AMCA), Texas Red™ (Molecular Probes, Inc., Eugene, Oreg.); 5-(and-6)-carboxy-X-rhodamine, lissamine rhodamine B, 5-(and-6)-carboxyfluorescein; fluorescein-5-isothiocyanate (FITC); 7-diethylaminocoumarin-3-carboxylic acid, tetramethyl-rhodamine-5-(and-6)-isothiocyanate; 5-(and-6)-carboxytetramethylrhodamine; 7-hydroxy-coumarin-3-carboxylic acid; 6-[fluorescein 5-(and-6)-carboxamido]hexanoic acid; N-(4,4-difluoro-5,7-dimethyl-4-bora-3a,4a diaza-3-indacenepropionic acid; eosin-5-isothiocyanate; erythrosine-5-isothiocyanate; 5-(and-6)-carboxyrhodamine 6G; Cascade™ blue aectylazide (Molecular Probes, Inc., Eugene, Oreg.), SpectrumOrange™, SpectrumAqua™, SpectrumGreen™, SpectrumGold™, and SpectrumRed™ (Vysis, Inc., Downers Grove, Ill.).

When multiple probes are used, fluorophores of different colors can be chosen such that each chromosomal probe in the set can be distinctly visualized. Preferably the probe panel of the invention will comprise four separate probes, each labeled with a separate fluorophore. It is also within the scope of the invention to use multiple panels sequentially on the same sample: in this embodiment, after the first panel is hybridized, the results are imaged digitally, the sample is destained and then is hybridized with a second panel. Probes can be viewed with a fluorescence microscope and an appropriate filter for each fluorophore, or by using dual or triple band-pass filter sets to observe multiple fluorophores. See, e.g., U.S. Pat. No. 5,776,688 to Bittner, et al., which is incorporated herein by reference. Any suitable microscopic imaging method can be used to visualize the hybridized probes, including automated digital imaging systems, such as those available from MetaSystems or Applied Imaging. Alternatively, techniques such as flow cytometry can be used to examine the hybridization pattern of the chromosomal probes.

Probes can also be labeled indirectly, e.g., with biotin or digoxygenin by means well known in the art. However, secondary detectable markers or further processing are then required to visualize the labeled probes. For example, a probe labeled with biotin can be detected by avidin conjugated to a detectable marker, e.g., a fluorophore. Additionally, avidin can be conjugated to an enzymatic marker such as alkaline phosphatase or horseradish peroxidase. Such enzymatic markers can be detected in standard colorimetric reactions using a substrate for the enzyme. Substrates for alkaline phosphatase include 5-bromo-4-chloro-3-indolylphosphate and nitro blue tetrazolium. Diaminobenzoate can be used as a substrate for horseradish peroxidase. Fluorescence detection of a hybridized biotin or other indirect labeled probe can be achieved by use of the commercially available tyramide amplification system.

The present invention is additionally described by way of the following illustrative, non-limiting Examples that provide a better understanding of the present invention and of its many advantages.

EXAMPLES

Example 1

Collection of Patient Samples and Cytological Screening 59 previously stained and routinely diagnosed Pap smear samples from 34 patients were collected from the archive of the Laboratory of Cytopathology at the Klinik Kloster Paradiese in Soest, Germany, with informed consent, and assigned to three groups. The Pap smears were evaluated according to established routine diagnostic procedures, i.e., initial screening by a cytotechnologist, and—when aberrant cells were found—a consensus diagnosis by two cytopathologists.

In brief, all samples were stained according to standard procedures and were embedded in a permanent mounting medium under coverslips. Cytological images were acquired from the samples. From cytologically normal lesions, 15-30 brightfield images were taken from areas on the slides that contained epithelial cells with reasonable cell density. If, during the screening process of normal Pap smears, cells that appeared suspicious were encountered, images were taken of these, as well. From the CIN lesions and the carcinomas, between 15 and 30 images were acquired from areas that contained phenotypically suspicious cells using a 20× Leica Phase contrast dry objective (NA 0.5). The xy coordinates of these areas were recorded.

Cytological grading was performed according to a custom classification system in Germany. Table 1 presents the conversion of the German classification system (based on the Munich nomenclature)[13] to the Bethesda nomenclature[14] and the nomenclature using cervical intraepithelial neoplasias.

TABLE 1

| Comparison of terminology: Cytological classification systems | | |
|---|---|---|
| Bethesda classification | Cervical intraepithelial neoplasia (CIN) | Pap I-V (used in Germany) |
| Normal | Normal | Pap I, Pap II |
| ASCUS | ASCUS | Pap IIw, Pap III |
| LSIL (low-grade squamous intraepithelial lesion) | CIN 1 | Pap IIID |
| HSIL (high-grade squamous intraepithelial lesions) | CIN 2<br>CIN 3 | Pap IVa, Pap IVb |
| Carcinoma | Carcinoma | Pap V |

The patient groups were as follows: the first patient group (n=22 samples) consisted of 12 cases for which the initial diagnosis was CIN1 and CIN2 (PapIIId). Matched Pap smears screened two months to two years after the initial diagnosis revealed progression to CIN3 (PapIV). This group was selected to evaluate whether CIN1 and CIN2 lesions that progress to CIN3 already carry extra copies of chromosome arm 3q.

The second group (n=19 samples) consisted of 10 cases wherein Pap smears were assessed as CIN1 or CIN2, and whose subsequent Pap smears, several months to two years later, were cytologically normal. It was hypothesized that the CIN1 and CIN2 lesions in this group would not have acquired gains of 3q.

The third group (n=23 samples) consisted of 12 cases for whom the Pap smears were initially diagnosed as normal. However, in all instances, these women developed CIN3 (PapIVa/b) (n=11) or cervical carcinomas (PapV) (n=1) after a follow-up period of only one to three years. In this group, it would be of interest to learn whether some of the normal Pap smears were already initially positive for 3q gain and to assess why cytological screening had not identified aberrant cells.

Example 2

FISH and Signal Enumeration

Prior to in situ hybridization, the coverslips were removed by incubating the slides in xylene for 2-4 days. After removal of the coverslips, the slides were washed twice in xylene, rehydrated, and de-stained in 0.5% HCl/70% EtOH for 1-2 hours. Slides were pre-treated with 0.05% pepsin for 10-30 minutes and fixed in 100% EtOH.

The three color fluorescent probe panel has been previously described.[8] It consists of a BAC contig that contains the human telomerase gene (TERC, labeled with SpectrumOrange™), a centromere enumeration probe for chromosome 3 (CEP3, labeled with SpectrumGreen™), and a control probe for the centromere of chromosome 7 (CEP7, labeled with SpectrumAqua™). The probe set is depicted schematically in FIG. 1.

Details of the hybridization conditions and post-hybridization washes were previously described.[8] The probes were provided by Vysis, Inc./Abbott Laboratories (Downers Grove, Ill.). About one third of the samples were hybridized using a probe cocktail provided by Cancer Genetics, Inc. (Milford, Mass.). In this probe set, the Spectrum Orange labeled TERC probe was replaced with a BAC contig specific for TERC that was directly labeled with rhodamine using the protocol developed by Kreatech (www.kreatech.com). In brief, this protocol relies on the use of a molecule consisting of a platinum complex, a detectable molecule, and a leaving group, which is displaced upon reaction with the target. The molecule forms a co-ordinative bond, firmly coupling it to the target. The performance of the probe sets was comparable (data not shown).

After hybridization, the cell nuclei were counterstained with DAPI and embedded in an antifade solution. Details of the FISH procedure, which can also be retrieved at www.riedlab.nci.nih.gov, are as follows: the hybridized slides were washed in 50% formamide/2×SSC (pH 7-7.5) for 3×5 min at 45° C., shaking. The slides were washed in 0.1×SSC at 45° C. for 3×5 min, shaking. The slides were dipped in 4×SSC/0.1% Tween 20. 120 µL Blocking Solution (3% BSA/4×SSC/0.1% Tween 20) were added to the slides, which were then covered with a 24 mm×60 mm coverslip in a moist hybridization chamber at 37° C. for 30 min.

The slides were dipped in 4×SSC/0/15 Tween 20 to wash off the blocking solution. The slides were stained for 5 min in DAPI staining solution in a light-protected coplin jar. The slides were washed for 5 min in 2×SSC, shaking. The slides were then dehydrated by dipping through an ethanol series of:

70%, 90%, and 100% and air-dried. Finally, 35 μL of antifade solution (1,4-phenylene-diamine-based) were applied, the slides were covered with 24 mm×60 mm coverslips and stored in a light-protected container at 4° C. until imaging of the slide.

After relocation, FISH images were acquired using a 40× Leica oil immersion objective (NA 1.25). Representative images of both cytology and FISH results are displayed in FIG. 2. In order to acquire images for the identical area on the slides, several fluorescent images were taken. Different numbers of cells were evaluated per case: this number was dependent upon cell density and on the number of morphologically aberrant cells (as identified by prior Pap staining). Signal enumeration was primarily focused on those cells that appeared suspicious by routine cytological screening (see examples in FIG. 2). The signal enumeration procedure therefore differed from the one previously described.[8] Cases were considered positive for the 3q assay when more than 20% of the cells exhibited a TERC signal number greater than 2.

Successful analysis of sequential samples was possible in 12 of 22 cases in group 1, in 10 of 19 cases in group 2, and in 12 of 23 cases in group 3. The morphological images that were acquired before FISH were reviewed and evaluated independently by two cytopathologists to ensure a direct correlation of the genetic with the cytological diagnosis. In the few cases of minor discordance between the two pathologists, a consensus diagnosis was achieved.

The results are summarized in Tables 2-4.

TABLE 2

Group 1: Progressors with 3q positive PAPIIID. Patient case number, date of birth, Pap smear dates, hybridization patterns, review diagnosis, and 3q status for the Pap IIID and the subsequent Pap IVa in patient.

| Case No. | Date of Birth | Date of Pap IIID | Review Diagnosis (consensus diagnosis of two pathologists evaluating the Pap images corresponding to the areas that hybridized with 3q) | Hybridization patterns observed in the Pap IIID and the number of nuclei counted for each pattern Patterns are described in the following order: CEP7-CEP3-3q | 3q status |
|---|---|---|---|---|---|
| 1 | Jan. 30, 1964 | October 2000 | Pap IVa, CIN3 | 1x 2-2-4, 1x 2-2-3, 3x ?-?-3, 1x 3-3-3, 1x 5-5-5, 1x ?-?-5 | Gain |
| 2 | Dec. 12, 1947 | August 2000 | Pap IIID, CIN 2 | 14x 2-2-3, 1x 2-3-3, 13x 3-3-3 | Gain |
| 3 | Mar. 27, 1968 | June 2001 | Pap IIID, CIN 2 | 3x 2-3-3, 2x 2-3-3 or 4, 2x 2-3-4, 3x 2-4-4, 2x 3-3-3 | Gain |
| 4 | Jan. 21, 1962 | January 2001 | Pap IIID, CIN 2 | 6x 2-2-5, 10x 2-2-6, 4x 2-?-4 or 5 | Gain |
| 5 | Sep. 21, 1959 | June 2000 | Pap IIID, CIN 2 | 6x ?-2-2, 18x ?-3-4, 5x ?-2-4, 6x ?-?-4 | Gain |
| 6 | Oct. 25, 1954 | July 2000 | Pap IIID, CIN 2 | 20x 2-2-2, 2x 2-2-3, 2x 2-3-4, 5x 3-4-4, 4x 3-4-5 | Gain |
| 7 | Jul. 5, 1960 | October 2000 | Pap IIID, CIN 2 | 10x 2-2-2, 12x 2-3-3, 2x 2-4-4 | Gain |
| 8 | Jan. 7, 1961 | December 1997 | Pap IIID, CIN 2 | 11x 2-2-2, 1x 2-2-3, 1x 2-4-4, 8x 4-4-4, 1x 4-4-5 | Tetraploid |
| 9 | 74 | 1997 | Pap IIw, ASCUS | 2x 2-2-2, 1x 2-2-4, 4x 4-4-4 | Tetraploid |
| 10 | Jun. 11, 1962 | October 1998 | Pap IIID, CIN 2 | 42x 4-4-4, 1x 3-3-3? | Tetraploid |
| 11 | Dec. 28, 1957 | March 1997 | Pap IIID, CIN 2 | 5x 2-2-2, 5x 4-4-4 | Tetraploid |
| 12 | Sep. 24, 1961 | 1999 | Pap IIID, CIN 2 | 2x 2-2-2, 29x 4-4-4, 1x 4-4-4 or 5 | Tetraploid |

| Case No. | Date of Pap IVa | Review Diagnosis (consensus diagnosis of two pathologists evaluating the Pap images corresponding to the areas that hybridized with 3q) | Hybridization patterns observed in the Pap IVa and the number of nuclei counted for each pattern Patterns are described in the following order: CEP7-CEP3-3q | 3q status |
|---|---|---|---|---|
| 1 | December 2000 | Pap IVa, CIN3 | 5x 2-3-3, 1x 3-3-3, 1x 3-4-4, 1x 4-5-5 | Gain |
| 2 | October 2000 | Pap IVa, CIN3 | 9x 2-2-3, 3x 2-3-3, 14x 3-3-3 | Gain |
| 3 | September 2001 | Pap IVa, CIN3 | 53x 2-2-3, 4x 2-3-3, 4x 2-3-4, 1x 2-2-5, 5x 3-3-3 | Gain |
| 4 | March 2001 | Pap IVa, CIN3 | 5x ?-?-6, 4x ?-?-5 or 6 | Gain |
| 5 | July 2001 | Pap IVa, CIN3 | 9x 2-2-2, 1x 2-2-3, 3x 2-3-3, 2x 2-2-4, 5x 2-3-4 | Gain |
| 6 | September 2000 | Pap IVa, CIN3 | 1x ?-?-2, 2x ?-?-4, 2x 2-?-5, 11x 3-?-5, 2x ?-?-5, 1x 3-?-6 | Gain |
| 7 | 2003 | Pap IVa, CIN3 | n.d. | n.d. |
| 8 | February 1998 | Pap IVa, CIN3 | 1x 3-3-3, 1x 3-4-4, 7x 4-4-4, 1x 4-4-5, 4x 4-5-5, 2x 5-5-5 | Gain |
| 9 | January 1999 | Pap IVa, CIN3 | 2x 2-2-2, 2x 3-4-4, 15x 4-4-4, 1x 4-4-5, 2x 4-4-4 or 5, 2x 4-5-5, 1x 4-4-6, 1x 5-5-5 | Gain |
| 10 | December 1999 | Pap IVa, CIN3 | 17x 4-4-4, 5x 4-5-5, 1x 5-5-5 | Gain |
| 11 | July 1997 | Pap IVa, CIN3 | 13x 2-2-2, 6x 4-4-4 | Tetraploid |
| 12 | July 2001 | Pap IVa, CIN3 | 4x 2-2-2, 17x 4-4-4, 1x 4-4-5? | Tetraploid |

"Main patterns" are marked in bold
"n.d." not determined

Table 2. Shown are the hybridization patterns and number of cells with a specific hybridization pattern observed in individual Pap smears. The column "3q status" reflects the interpretation of the hybridization patterns as it pertains to 3q copy numbers Nine of the 12 CIN3 lesions in group 1 (Table 2: progressors) revealed varying degrees of cells with extra copies of chromosome arm 3q, and two were tetraploid (hybridization pattern of four signals for all three probes, 4-4-4); one case was not determined. Seven of the preceding matched CIN1 and CIN2 lesions were positive for 3q gain, as well, indicating that those CIN1/CIN2 lesions with a high likelihood for progression frequently carry extra copies of this genetic marker. The remaining five lesions were tetraploid, including the precursors of the two tetraploid CIN3 lesions.

Table 3. Shown are the hybridization patterns and number of cells with a specific hybridization pattern observed in individual Pap smears. The column "3q status" reflects the interpretation of the hybridization patterns as it pertains to 3q copy numbers In group 2 (Table 3: regressors), seven of the non-progressing CIN1/CIN2 lesion were diploid (hybridization pattern of two signals each for all probes, 2-2-2); three cases were tetraploid (4-4-4), and none of the cases showed a gain of 3q. These findings demonstrate that CIN1/CIN2 lesions that spontaneously regress do not carry a gain of TERC.

TABLE 3

Group 2: Regressors. Patient case number, date of birth, Pap smear dates, hybridization patterns, review diagnosis, and 3q status for the Pap IIID and the subsequent normal Pap smear of patient.

| Case No. | Date of Birth | Date of Pap IIID | Review Diagnosis (consensus diagnosis of two pathologists evaluating the Pap images corresponding to the areas that hybridized with 3q) | Hybridization patterns observed in the Pap IIID and the number of nuclei counted for each pattern Patterns are described in the following order: CEP7-CEP3-3q |
|---|---|---|---|---|
| 1 | ######## | October 1999 | Pap IIID, CIN 2 | 29x 2-2-2 |
| 2 | Sep. 3, 1959 | January 2001 | Pap IIID, CIN 2 | 25x 2-2-2, 1x 2-3-3? |
| 3 | Mar. 28, 1969 | 2000 | Pap IIID, CIN1/2 | 40x 2-2-2 |
| 4 | Apr. 6, 1969 | 2000 | Pap IIID, CIN 2 | 46x 2-2-2, 3x 4-4-4, 1x 4-4-4? |
| 5 | Jun. 5, 1977 | July 1999 | Pap IIID, CIN 2 | 49x 2-2-2, 1x 2-2-3?, 1x 2-2-4, 2x 4-4-4 |
| 6 | Feb. 28, 1970 | February 1999 | Pap IIID, CIN1/2 | 57x 2-2-2, 1x 2-2-3?, 3x 2-2-4 |
| 7 | Apr. 15, 1947 | August 1999 | Pap IIID, CIN 2 | 19x 2-2-2, 2x 4-?-4, 1x ?-?-4 or 5 |
| 8 | ######## | 1999 | Pap IIID, CIN 1/2 | 18x 2-2-2, 1x 2-2-4, 4x 4-4-4, 1x 4-?-4 |
| 9 | Aug. 1, 1954 | 2000 | Pap IIID, CIN 1 | 50x 2-2-2, 1x 2-2-4?, 13x 4-4-4 |
| 10 | Sep. 14, 1973 | February 2001 | Pap IIID, CIN 2 | 10x 2-2-2, 7x 4-4-4, 1x 4-?-4 |

| Case No. | 3q status | Date of Pap II | Review Diagnosis (consensus diagnosis of two pathologists evaluating the Pap images corresponding to the areas that hybridized with 3q) | Hybridization patterns observed in the Pap II and the number of nuclei counted for each pattern Patterns are described in the following order: CEP7-CEP3-3q | 3q status |
|---|---|---|---|---|---|
| 1 | Diploid | August 2000 | Pap I, normal | 34x 2-2-2 | Diploid |
| 2 | Diploid | 2001 | n.d. | not evaluable | n.d. |
| 3 | Diploid | December 2000 | n.d. | n.d. | n.d. |
| 4 | Diploid | 2001 | n.d. | not evaluable | n.d. |
| 5 | Diploid | December 1999 | n.d. | not evaluable | n.d. |
| 6 | Diploid | 2000 | n.d. | n.d. | n.d. |
| 7 | Diploid | July 2001 | Pap II, normal | 20x 2-2-2 | Diploid |
| 8 | Tetraploid | April 2000 | n.d. | not evaluable | n.d. |
| 9 | Tetraploid | 2001 | n.d. | n.d. | n.d. |
| 10 | Tetraploid | 2001 | n.d. | not evaluable | n.d. |

"Main patterns" are marked in bold

"n.d." not determined

| Case No. | Date of Birth | Date of Pap I/II | Review Diagnosis (consensus diagnosis of two pathologists evaluating the Pap images corresponding to the areas that hybridized with 3q) | Hybridization patterns observed in the Pap I/II and the number of nuclei counted for each pattern Patterns are described in the following order: CEP7-CEP3-3q | 3q status |
|---|---|---|---|---|---|
| 1 | Sep. 22, 1941 | Pap I: 1999 | Pap I/II, normal | 17x 2-2-2, 1x 2-2-3?, 1x 2-3-3? | Diploid |
| 2 | ######## | Pap II: 1999 | Pap II, normal | 14x 2-2-2, 1x 2-2-3?, 1x 2-3-3? | Diploid |
| 3 | Jul. 8, 1958 | Pap I: October 1996 | Pap II, normal | 15x 2-2-2, 2x 2-2-3? | Diploid |
| 4 | Apr. 16, 1951 | Pap I: Sept 97 | Pap II, normal | 16x 2-2-2, 1x 2-4-4?, 1x 3-3-3? | Diploid |
| 5 | Jun. 17, 1973 | Pap II: February 1998 | Pap II, normal | 34x 2-2-2, 1x 2-3-3? | Diploid |
| 6 | ######## | Pap II: March 00 | Pap IIID, CIN1 | 22x 2-2-2, 1x 5-5-5? | Diploid |
| 7 | ######## | Pap I: July 2001 | Pap I, normal | 22x 2-2-2, 2x ?-?-3? | Diploid |
| 8 | Feb. 28, 1967 | Pap II: 1998 | Pap II, normal | 18x 2-2-2 | Diploid |
| 9 | Sep. 23, 1961 | Pap II: July 97 | Pap II, normal | 20x 2-2-2, 1x 2-3-3?, 16x 2-3-4, 2x 2-3-5 | Gain |
| 10 | Jul. 13, 1950 | Pap I: 1996 | Pap IIID, CIN 2 | 3x 2-2-2, 4x 2-?-3, 1x 2-2-3, 3x 2-?-4, 1x 2-2-4, 3x 2-?-5, 1x 2-2-5, 2x 2-5-5, 1x2-2-6, 1x 2-?-7, 1x 3-?-4, 2x 4-4-4 | Gain |
| 11 | ######## | Pap II: 1997 | Pap IVa, CIN 3 | 8x 2-2-2, 46x 2-5-5 | Gain |
| 12 | May 18, 2015 | Pap II: August 1998 | Pap II, normal | 52x 2-?-2, 15x 2-?-3, 3x 2-2-3, 2x 4-?-4, 1x 4-?-8 | Gain |

| Case No. | Date of Pap IVa/IVb | Review Diagnosis (consensus diagnosis of two pathologists evaluating the Pap images corresponding to the areas that hybridized with 3q) | Hybridization patterns observed in the Pap IVa/b and the number of nuclei counted for each pattern Patterns are described in the following order: CEP7-CEP3-3q | 3q status |
|---|---|---|---|---|
| 1 | Pap IVb: February 2001 | Pap IVb, CIN3 | 4x 2-2-3, 2x 2-3-3, 1x 3-3-3, 1x 2-3-4, 1x 2-5-5, 3x 3 5-5, 4x 4-5-5 | Gain |
| 2 | Pap IVa: May 00 | Pap IVa, CIN3 | 5x 2-2-3, 5x 2-3-3, 3x 2-4-4, 3x 4-4-4, 1x 5-4-4 | Gain |
| 3 | Pap IVa: January 1999 | Pap IVa, CIN3 | 1x 2-2-2, 6x 2-2-3, 3x 2-3-3, 1x 2-2-4, 1x 2-3-4 | Gain |
| 4 | Pap IVa: June 98 | Pap IVa, CIN3 | 4x 2-2-2, 2x 2-2-3, 6x 2-3-3, 1x 2-3-4, 2x 3-3-3, 2x 3 3-4, 1x 3-3-5, 1x 4-4-4, 4x 3-3-? | Gain |
| 5 | Pap IVa: February 1999 | Pap IVa, CIN3 | 18x 2-2-2, 6x 2-2-3, 4x 2-3-3, 1x 3-3-3 | Gain |
| 6 | Pap IVa: August 2001 | Pap IVa, CIN3 | 1x 2-2-2, 2x 3-4-4, 7x 4-4-4, 4x 4-5-5, 9x 5-5-5 | Gain |
| 7 | Pap IVb: April 02 | Pap IVb, CIN3 | 9x ?-?-3, 4x ?-3-3, 2x 2-3-3 | Gain |
| 8 | Pap IVa: June 00 | Pap IVa, CIN3 | 61x 4-4-4, 1x 2-2-3?, 3x 4-4-5?, 1x 3-4-4? | Tetraploid |
| 9 | Pap IVa: March 00 | Pap IVa, CIN 3 | 2x 2-2-2, 3x 2-3-3, 98x 2-3-4, 1x 2-3-5, 2x 2-4-5, 4x 4-6-6 | Gain |
| 10 | Pap V: April 99 | Pap IVa, CIN 3 | 4x 2-2-2, 1x 2-2-3, 3x 2-3-3, 6x 2-2-4, 8x 2-2-5, 8x 2-2-6, 1x 2-2-7, 3x 2-2-8, 26x 2-4-4, 1x 2-4-5, 1x 2-4-6, 1x 2-4-5, 13x 2-5-5, 1x 2-4-6, 1x 2-6-9, 1x 3-3-3, 10x 3-4-4, 1x 3-3-5, 1x 3-3-6, 1x 3-3-7, 1x 3-4-5, 1x 3-5-7, 1x 3-6-6, 3x 4-4-4 | Gain |
| 11 | Pap IVa: August 1999 | Pap IVa, CIN 3 | 6x 2-2-2, 5x 2-4-4, 128x 2-5-5 | Gain |
| 12 | Pap V: February 1999 | Pap V, Carcinoma | 6x 2-2-2, 10x 2-2-3, 1x 3-2-3, 3x 2-3-5, 1x 2-2-8, 1x 2-3-8, 1x 3-3-8, 87x 4-3-8, 1x 4-4-5, 1x 4-4-8, 1x 5-4-8 | Gain |

"Main patterns" are marked in bold

Table 4. Shown are the hybridization patterns and number of cells with a specific hybridization pattern observed in individual Pap smears. The column "3q status" reflects the interpretation of the hybridization patterns as it pertains to 3q copy numbers Eleven of the 12 CIN3 lesions and carcinomas in group 3 (Table 4: normal Pap smear followed by CIN3 or carcinoma) revealed a 3q gain. One lesion (#8, Table 4) was tetraploid. Of note, four of the 12 cytologically normal Pap smears already exhibited a gain of 3q. This indicates that the visualization of additional copies of the TERC gene could serve as an early and specific marker in cytologically normal Pap smears obtained from women who are prone to develop CIN3 lesions or invasive disease.

Of note, a certain number of cases in the groups of progressors and regressors showed signal patterns that are compatible with a tetraploidization of the genome (i.e., four copies of CEP7, CEP3, and 3q, referred to as 4-4-4 in Tables 2-4). The hybridization patterns observed in the 3q-positive CIN3 lesions and their matched CIN1/2 precursors suggest that a certain chromosomal aneuploidy, once established, is maintained during tumor progression, which again suggests clonal expansion (Tables 2-4). It is striking that none of the 3q-positive lesions in which the gain of TERC occurred on a diploid background (as assessed with the copy numbers for CEP3 and CEP7) showed a tetraploid hybridization pattern at lower-grade lesions.

All CIN3 lesions for which the corresponding premalignant lesions were tetraploid, maintained tetraploidy or developed 3q gain on a tetraploid background. This observation indicates that the gain of 3q can occur on the basis of either a diploid or tetraploid genome. Thus, quantitative DNA content measurement alone may not suffice as a diagnostic method in cervical cytology.[30]

While none of the samples in group 2 (regressors) were positive for 3q gain, three lesions were tetraploid. This implies that tetraploidization per se does not modify the genome such that progression is unavoidable. This is consistent with previous observations indicating that genome duplication can occur as a physiological response to certain environmental challenges.[30,31]

In the review diagnosis of the morphological images by two experienced cytopathologists, one of the four 3q positive lesions was upgraded from normal to CIN2 (Pap IIID), and another one was upgraded to CIN3 (Pap IVa), whereas the diagnosis for two of them remained as previously determined, i.e., normal.

The comparison of the cytological phenotype of the cells with the genetic makeup indicates that, in two cases, the dysplastic cells were present on the slide, yet were indeed overlooked (a known problem in cervical cytology); however, in two other cases, the cellular phenotype appeared normal on review despite the presence of chromosomal aneuploidy and gain of 3q. This demonstrates that the acquisition of specific genomic gains can precede phenotypic alterations appreciable by morphological inspection. Examples of images of these cases are displayed in FIG. 2.

Figure 2A:
FIG. 2A shows the results of the hybridization of the TERC gene (red) to previously stained routine Pap smears from patient 9 (group 2, regressors, Table 3). Two distinct areas of the slide are visualized. For simplicity, only the signals for the TERC probe are shown. All nuclei exhibit two TERC signals indicating a normal diploid status for these cells.
Figure 2B:
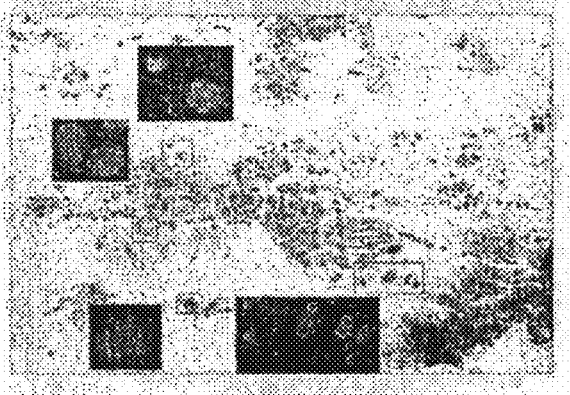
FIG. 2B shows the results of the hybridization of the TERC gene (red) to previously stained routine Pap smears from patient 2 (group 1, progressors, Table 2). Multiple nuclei that appeared aberrant during the cytological screening throughout the slide reveal extra copies of TERC (shown as red signals). Note that both larger nuclei and cells with small nuclei reveal increased copy numbers for this gene (lower right area).
Figure 2C:
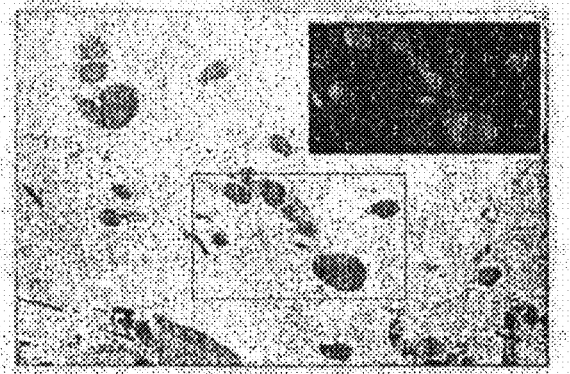
FIG. 2C shows the results of the hybridization of the TERC gene (red) to previously stained routine Pap smears from patient 7 (group 1, Table 2). Note multiple 3q-positive cells in the Pap smear (main pattern 2-3-3).
Figure 2D:
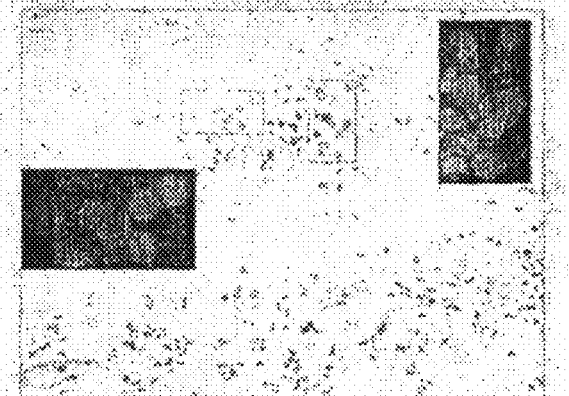
FIG. 2D shows the results of the hybridization of the TERC gene (red) to previously stained routine Pap smears from patient 9 (group 3, Table 4). This case revealed four, occasionally five copies of 3q on a diploid background (i.e., two signals for CEP7). Interestingly, the subsequent CIN3 lesion showed the same main pattern (2-3-4), supporting the hypothesis of clonal expansion.

FIG. 2A corresponds to a Pap smear assessed as Pap IIID (CIN1). Of note, the morphologically suspicious cells do not carry extra copies of the TERC genes (two copies per cell only). FIG. 2B corresponds to a Pap smear assessed as Pap IIID (CIN2). FIG. 2C corresponds to the Pap smear of a patient initially diagnosed as Pap IIID (October 2000) and considered a regressor because subsequent Pap smears were normal (2001), but assessed via a 2002 Pap smear as CIN2 and via a 2003 Pap smear as CIN3 (and, accordingly, assigned to group 1). FIG. 2D corresponds to a Pap smear repeatedly judged as morphologically normal, though the patient presented with a CIN3 lesion after 28 months.

Of note, in many instances, the cells that were positive for additional copies of 3q were located next to each other on the diagnostic slides. This indicates a clonal evolution event, where extra copies of 3q render a growth advantage to cervical epithelial cells, which eventually results in a cell population in cervical carcinomas in which the majority of the cells are positive for 3q. Accordingly, visualization of additional copies of the TERC gene in premalignant dysplastic lesions is not only informative for the diagnosis of dysplasia, but can also provide information regarding the progressive potential of individual lesions.

The review diagnosis of the morphological images of the areas evaluable with the 3q marker was in concordance with the initial diagnosis for 53 out of the 59 specimens (90%). Six specimens were up- or downgraded from the original diagnosis, including the cases discussed above (Group 3, Table 4, case 10 from Pap I to Pap IIID, and case 11 from Pap II to Pap IVa). The original Pap V diagnosis of case 10 (Table 4) was downgraded to Pap IVa. In group 3, Table 4, case 6 was upgraded from Pap II to Pap IIID, and in group 1, Table 2, case 1 was upgraded from Pap IIID to Pap IVa, and case 9 was downgraded from Pap IIID to Pap IIw, ASCUS.

As hypothesized, some of the Pap smears that had previously been assessed as normal revealed the presence of 3q, the detection of which would have resulted in an earlier diagnosis. Indeed, seven of 12 CIN1/CIN2 lesions that progressed to CIN3 were found positive for 3q (all matched CIN3 lesions carried amplified TERC). In strong contrast, none of the spontaneously regressing lesions showed a 3q gain.

Example 3

Statistical Evaluation of Data

A. Fisher's Exact Test

The statistical evaluation was based on the Fisher's exact test and the exact binomial parameter estimation, which is suited for small sample numbers. The Fisher's exact test was used for 2×2 contingency table analysis of the categorical data. The two categorical variables used are the pathological assessment (progression and regression) and the detection of genomic aberrations, which is either positive or negative. Each cell in Table 5 reflects the observed outcomes from patient samples.

The null hypothesis ($H_0$) postulates that the presence of genomic aberrations (either the gain of 3q or tetraploidy) and the progression status are independent from one another. The progression rate is defined as the number of cases that progress over the total number of cases tested. The upper and lower endpoints of the exact confidence intervals for estimation of this binomial parameter were denoted as $P_L(\alpha)$ by $P^\alpha_L(n,B)$ and $P_U(\alpha)$ by $P^\alpha_u(n, B)$ and were determined based on the equations below.[15]

$$P^\alpha_L(n, B) \frac{B}{B + (n - B + 1)f_{\alpha/2, 2(n-B+1), 2B}}$$

and $$P^\alpha_u(n, B) = 1 - P^\alpha_L(n, n - B)$$

B refers to the number of progressions (successes) in the n Bernoulli trials, and $f_{\gamma, n_1, n_2}$ is the upper $\gamma^{th}$ percentile for the F distribution with $n_1$ degree of freedom in the numerator and $n_2$ degrees of freedom in the denominator.

The results are summarized in Table 5.

TABLE 5

Statistical evaluation

| Aberration profile | Pathological assessment | | p-value from Fisher's test | Progression rate | 95% confidence interval of progression rate | |
|---|---|---|---|---|---|---|
| | Progression | Regression | | | lower | upper |
| 4-4-4 | 5 | 3 | 0.6749 | 0.625 | 0.2449 | 0.9148 |
| 2-2-2 and 3q gain | 7 | 7 | | 0.5000 | 0.2304 | 0.7696 |
| 3q gain | 7 | 0 | 0.0053 | 1.0000 | 0.5904 | 1.0000 |
| 2-2-2 and 4-4-4 | 5 | 10 | | 0.3333 | 0.1182 | 0.6162 |
| 3q gain and 4-4-4 | 12 | 3 | 0.0007 | 0.8000 | 0.5191 | 0.9567 |
| 2-2-2 | 0 | 7 | | 0.0000 | 0.0000 | 0.4096 |

Table 5. Statistical analysis for contingency tables and confidence intervals of the progression rate. From the left, the column classifier for all three 2×2 contingency tables is the pathological assessment (progression and regression). The row classifiers are the detection of tetraploidy (top 2×2 table), gain of the chromosome 3q (center 2×2 table) and gain of the 3q including tetraploidy (bottom 2×2 table), respectively. The two-tailed p-value for each table is derived from the Fisher's exact test. On the right, the progression rate for the different hybridization patterns was calculated based on the cell counts in the contingency tables. Its exact 95% confidence interval was obtained using the method described in the Materials and Methods section.

For the patients whose Pap smears contained tetraploid cells, the odds (5 to 3) are in favor of progression, yet the p-value is 0.6749. Therefore, $H_0$ cannot be rejected (i.e., there is no strong statistical evidence that tetraploidy is associated with progression).

For cases with a 3q gain versus diploid and tetraploid cases, the p value is 0.0053. Thus, there is strong evidence to reject $H_0$, indicating that additional copies of 3q and progression are associated. The 95% confidence interval ranges from 0.5904 to 1.0000. Thus, with 95% confidence, the probability of progression is expected to be 59% to 100%.

For patients that have either a gain of 3q or tetraploidy, the p value for the test is 0.0007. Therefore, $H_0$ can be rejected with confidence. A significant correlation exists between additional copies of 3q and carcinoma development. A 52% to 96% progression rate is expected in patients with either 3q-positive or tetraploid samples.

If the afore-mentioned cases in the groups of progressors and regressors that showed signal patterns that are compatible with a tetraploidization of the genome (see Example 2, above) are included using a conservative threshold of 20%, the test achieves a sensitivity of 100% (i.e., the association of progression with either tetraploidy or TERC gain) with a specificity of 70%, which is defined as the association of regression with the absence of 3q positive patterns, i.e. 3q gain including tetraploidy (seven of 10 cases, as per Table 5).

B. ROC Analysis

Receiver Operator Characteristic (ROC) analysis was used to further establish optimal thresholds and identify FISH parameters that best predicted progression. ROC curves were generated by plotting the sensitivity for predicting progression versus 1 minus the specificity for predicting regression, calculated at percent cell thresholds ranging from 0% to 100% (1% increments). Curves were generated based on the percentage of tetraploid cells (4-4-4 hybridization pattern), the percentage of cells with 3q gain (>2 TERC signals per cell, excluding tetraploidy), and the percentage of cells with either tetraploidy or 3q gain (i.e., >2 TERC signals per cell, including tetraploidy).

Figure 3A:
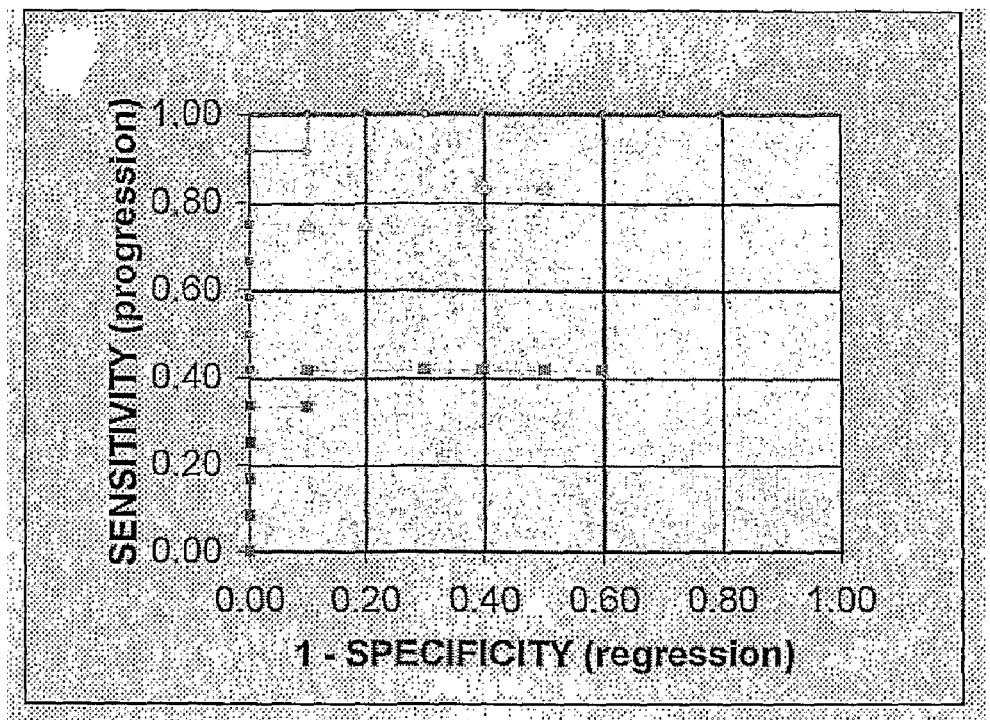
FIG. 3A shows the ROC plot of sensitivity versus 1—specificity at thresholds ranging between 0 and 100% abnormal cells for 3q gain.

In FIG. 3A, comparison of the ROC curves shows that tetraploidy alone (blue squares) is not a good indicator of progression, while 3q gain (defined for this purpose as >2 TERC signals/cell, exclusive of tetraploidy, white triangles) is a better indicator, and 3q gain including tetraploidy (any gain of 3q, red circles) shows very good ROC characteristics.

In the ROC plot, curves that come closest to the ideal values of 100% sensitivity and 100% specificity (top left corner of ROC graph, see FIG. 3A) provide the best combination of sensitivity and specificity (assuming equal importance of each), and optimal thresholds are typically selected from points near the 'breaks' in the curves (region closest to top left corner; curve slope near 45°).

The point on the latter ROC curve lying closest to the top left corner of the graph represents sensitivity and specificity values of 91.7% (11/12) and 100% (10/10), respectively, which are obtained for cell percentage thresholds of 45 to 49%. However, for identifying women likely to progress, higher sensitivity is preferred and 100% sensitivity (12/12) with 90% specificity (9/10) are achieved with thresholds ranging between 25 to 39%. To further ensure identification of likely progressors, a more conservative threshold of 20% was used in the present study.

C. DFI Analysis

Figure 3B:
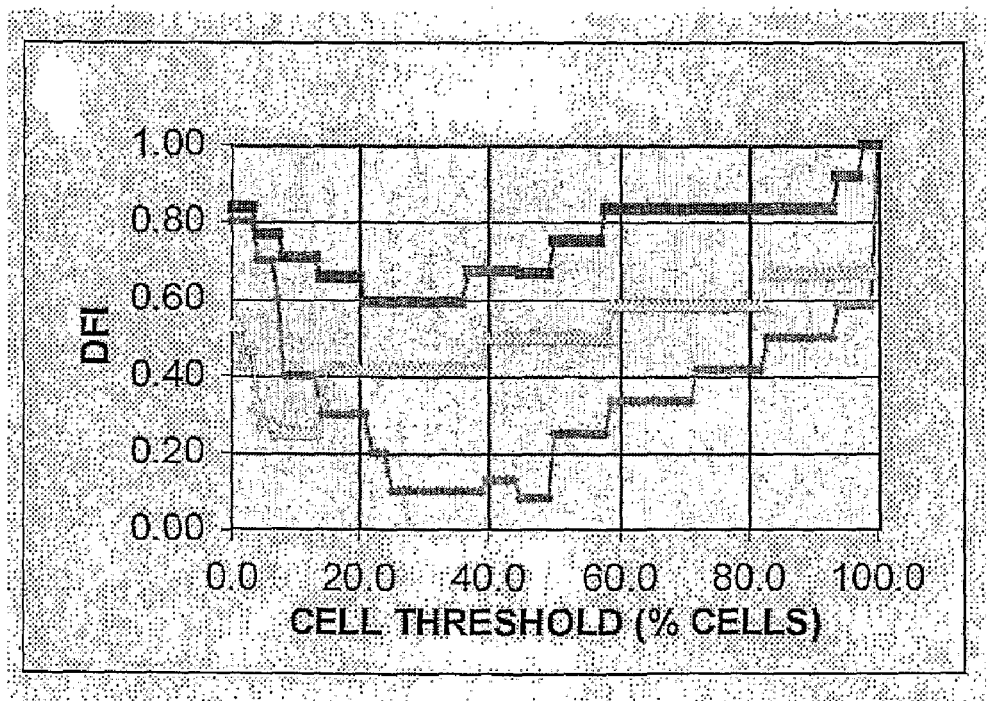
FIG. 3B shows the plot of DFI versus threshold for 3q gain. The white triangles in both 3A and 3B denote the results when considering cells with >2 TERC signals/cell, excluding tetraploidy as positive. The blue squares reflect the results when only tetraploid cell were considered, i.e., hybridization patterns of four signals for each probe (4-4-4). The red circles show the results when considering cells with any 3q gain (>2 TERC signals/cell including cells with a tetraploid hybridization pattern).

A better view of the dependence of sensitivity and specificity on threshold can be obtained by plotting the Distance From Ideal (DFI) versus threshold (FIG. 3B, which uses the same data used to construct FIG. 3A). DFI is defined as the distance from the ideal point (0, 1) on the ROC plot (100% sensitivity, 100% specificity) and is calculated as $[(1-\text{sensitivity})^2+(1-\text{specificity})^2]^{1/2}$. DFI is smallest for the best combined sensitivity and specificity (giving equal weight to each) and varies from a value of 0 for thresholds providing 100% sensitivity and 100% specificity, i.e., the ideal point to a maximum value of $2^{1/2}$.

The curves identify the threshold ranges providing the lowest combined sensitivities and specificities, and emphasize that 3q gain inclusive of tetraploidy (red circles) is better suited to predict progression (lowest and broadest minimum of the three curves) than tetraploidy alone (blue squares) or 3q gain alone (white triangles). Minima on a DFI curve indicate the best values for thresholds, and broad minima are indicative of more robust assays, since placement of thresholds is less critical.

Although the foregoing invention has been described in some detail by way of illustration and example for purposes of clarity and understanding, it will be apparent to those skilled in the art that certain changes and modifications can be practiced. Therefore, the description and examples should not be construed as limiting the scope of the invention, which is delineated by the appended numbered claims.

Example 4

Frequent Gain of TERC in Cervical Adenocarcinomas

Tumor Material

The study includes formalin-fixed paraffin embedded tumour tissue specimens from 12 primary cervical adenocarcinomas diagnosed and surgically treated at the Karolinska University Hospital-Huddinge during 1992-2000 (Table 6). All tumour cases were identified from the Swedish Central Cancer Registry organized by the National Board of Health and Welfare. This registry includes all cases of malignant tumours diagnosed histopathologically after 1959, whereby each tumour is identified by a topographical and histopathological code. All tumour samples were collected with informed consent and approval from the local ethics committee.

TABLE 6

Clinical details and HPV status of the 12 adenocarcinomas in the study.

| Case no | Lab id. | Cancer diagnosis | Last Pap smear year/result | Age at diagnosis | Tumor stage | Tumor differentiation | Lymph node involvement | HPV infection status | Follow-up time | outcome |
|---|---|---|---|---|---|---|---|---|---|---|
| 1 | 230-3 | 1992 | 1990/normal | 30 yrs | 1B | Poor | No | HPV 16 | 13 yrs | AwoD |
| 2 | T15-2 | 1992 | 1989/normal | 46 yrs | 1B | Poor | No | HPV 18 | 13 yrs | AwoD |
| 3 | 186-5 | 1995 | 1992/normal | 37 yrs | 1B | Well | No | HPV 18 | 10 yrs | AwoD |
| 4 | 120-7 | 1997 | 1987/normal | 39 yrs | 1B | Well | No | HPV negative | 8 yrs | AwoD |
| 5 | 549-3 | 1992 | 1978/normal | 50 yrs | 2B | Well | Yes | HPV negative | 13 yrs | AwoD |
| 6 | 149-4 | 1994 | 1992/normal | 32 yrs | 1B | Poor | No | HPV 18 | 11 yrs | AwoD |
| 7 | 162-0 | 2000 | 1997/normal | 62 yrs | 1B | Well | No | HPV 45 | 4 yrs | DoD |
| 8 | 164-0 | 2000 | 1998/normal | 64 yrs | 1B | Poor | No | HPV negative | 5 yrs | AwoD |
| 9 | 179-9 | 1999 | 1996/normal | 63 yrs | 2B | Moderate | Yes | HPV negative | 6 yrs | AwoD |
| 10 | 235-9 | 2000 | 1999/inflammation | 53 yrs | 1A | Well | No | HPV 16 | 5 yrs | AwoD |
| 11 | 062-7 | 1997 | 1996/normal | 45 yrs | 1B | Well | No | HPV 18 | 7 yrs | DoD |
| 12 | 132-3 | 1993 | 1992/normal | 49 yrs | 1A | Well | No | HPV 18 | 11 yrs | AwoD |

AwoD = Alive without disease;
DoD = Dead of disease

The clinical information for each case is detailed in Table 6 and has been previously published (Andersson et al, 2003a). The histopathological diagnosis was based on WHO criteria. The 12 tumours were classified as cervical adenocarcinomas and all were without any squamous cell component. Seven tumours were well differentiated (58%), one was moderately differentiated (8%) and four tumours were poorly differentiated (33%). Clinical staging was according to the FIGO classification for cervical cancer (Benedet et al, 2000). At initial diagnosis, 10 tumors were classified as stage I (83%), and two tumors as stage II (17%). Two patients initially exhibited lymph node involvement (17%). All patients were previously sampled for Pap smear analysis. All but one Pap smear (which was evaluated as showing signs of cellular inflammation) were assessed as normal at the time of the most recent cytological evaluation (Table 6). All patients were retrospectively followed-up from the time of diagnosis until June 2005, and disease recurrence and survival data recorded.

HPV Status

Results from HPV screening analyses have been previously published for all cases (Andersson et al, 2003a). Briefly, the analyses were performed on extracted DNA obtained from sections of paraffin blocks of which the preceding section had been used for morphological diagnosis. A fragment of 139-148 bp was amplified from the L1 region with GP5+/GP6+ primers, HPV-typed by direct DNA sequencing and comparison to known HPV sequence databases using the BLAST algorithm (www.ncbi.nlm.nih.gov/BLAST). Eight of the 12 tumours were thus found to be HPV-positive; five tumours were infected with HPV 18, two with HPV 16, and one with HPV 45 (Table 6). The remaining four tumour specimens were HPV-negative. The mean age at cancer diagnosis was significantly lower for the HPV-positive cases as compared to the HPV negative women (44.2 years, SD=10.4 vs. 54 years, SD=10.8; p=0.001).

Preparation of Nuclei Suspensions for FISH Analysis

Single layer nuclei preparations for interphase FISH hybridizations were prepared using the Hedley method with modifications (Castro et al, 1993). A 50 µm section was cut from each of the 12 formalin fixed paraffin-embedded tumour tissue samples. After deparaffinization in xylene, the section was rehydrated in an ethanol series and in distilled water, and the section was disintegrated in 500 µl of 0.1% Protease/1× PBS (Protease:Type XXIV, Bacterial, P 8038, Sigma St. Louis, Mo. and Dulbecco's 1×PBS, Life Technologies, Rockville, Md.) at 45° C. for 45-60 minutes. The reaction was stopped by adding 500 µl 1×PBS at room temperature. The sample was then filtered through a nylon membrane (CN 051, DAKO, Glostrup, Denmark) centrifuged and resuspended in 1×PBS. Cytospin slides were prepared by Shandon Cytospin®, and fixed in an ethanol series.

Fluorescence In Situ Hybridization (FISH)

Triple-color FISH analysis was performed on each case using the following probe set: a centromere specific probe for chromosome 7 (CEP®7); a centromere specific probe for chromosome 3 (CEP3); and a contig consisting of four overlapping BAC clones containing the TERC gene at chromosomal location 3q26. All probes were obtained from Vysis/Abbott Molecula, Inc. (Des Plaines, Ill.). The details for this probe set, its sensitivity and specificity, as well as experimental conditions were published previously (Heselmeyer-Haddad et al, 2003). In short, CEP7 was labeled with Spectrum Aqua™ (SA), CEP3 with Spectrum Green™ (SG) and the TERC contig with Spectrum Orange™ (SO), using chemical labeling as described (Bittner et al, 1996). Before hybridization, the cytospin slides were pretreated with a pepsin digestion, and fixed in an ethanol series. Slides were denatured in 70% formamide, 2×SSC for 3.5 minutes at 80° C. The probes were denatured according to the manufacturer's recommendations. After overnight hybridization at 37° C., the slides were first washed four times in 50% formamide/2×SSC at 45° C. (once for 3 minutes and three times for 7 minutes), followed by washes in 2×SSC at 45° C. for 5 minutes and in 2×SSC/0.1% NP40 at 45° C. for 5 minutes. The slides were counterstained with 4,6-diamidino-2-phenylindole (DAPI), and subsequently embedded in an antifade solution.

Scoring of FISH Results

FISH and image analyses were carried out using a Leica DM-RXA fluorescence microscope (Leica, Wetzlar, Germany) equipped with custom optical filters for DAPI, SA, SG and SO (Chroma Technologies, Brattleboro, Vt.) and 40× Plan Apo (NA 1.25) objective. Images were taken in areas of optimal cell density with minimal cellular clumps using an ORCA ER (IEEE1394 I/F) digital camera (Hamamatsu, Bridgewater, N.J.). Leica Q-Fluoro was used to acquire multifocus images for each of the DAPI, SA, SG and SO optical filters. Ten to 16 images were acquired and signal enumeration was performed on these digital images for 208-641 nuclei for each case. The counted signals were listed and evaluated in Excel based customized software.

Nuclei that could not be evaluated (e.g., because of insufficient hybridization or overlapping nuclei) were excluded from further analysis. The results for all "countable" nuclei were registered in relocation charts in form of patterns for the entire probe panel. For example, the pattern (2-3-3), refers to two signals for CEP7, three signals for CEP3 and three signals for TERC in a given nuclei. Nuclei with normal signal numbers for the three probes (i.e., 2-2-2) were recorded as "diploid", and nuclei with four signals for each probe (pattern 4-4-4) were considered "tetraploid". The background level for the CEP7-CEP3-TERC probe panel was previously evaluated on cytological slides that contained nuclei from normal cervical cells (Heselmeyer-Haddad et al, 2003). This confirmed that deviation from the expected (2-2-2) pattern was seen in less than 2% of normal cells.

Figure 4:
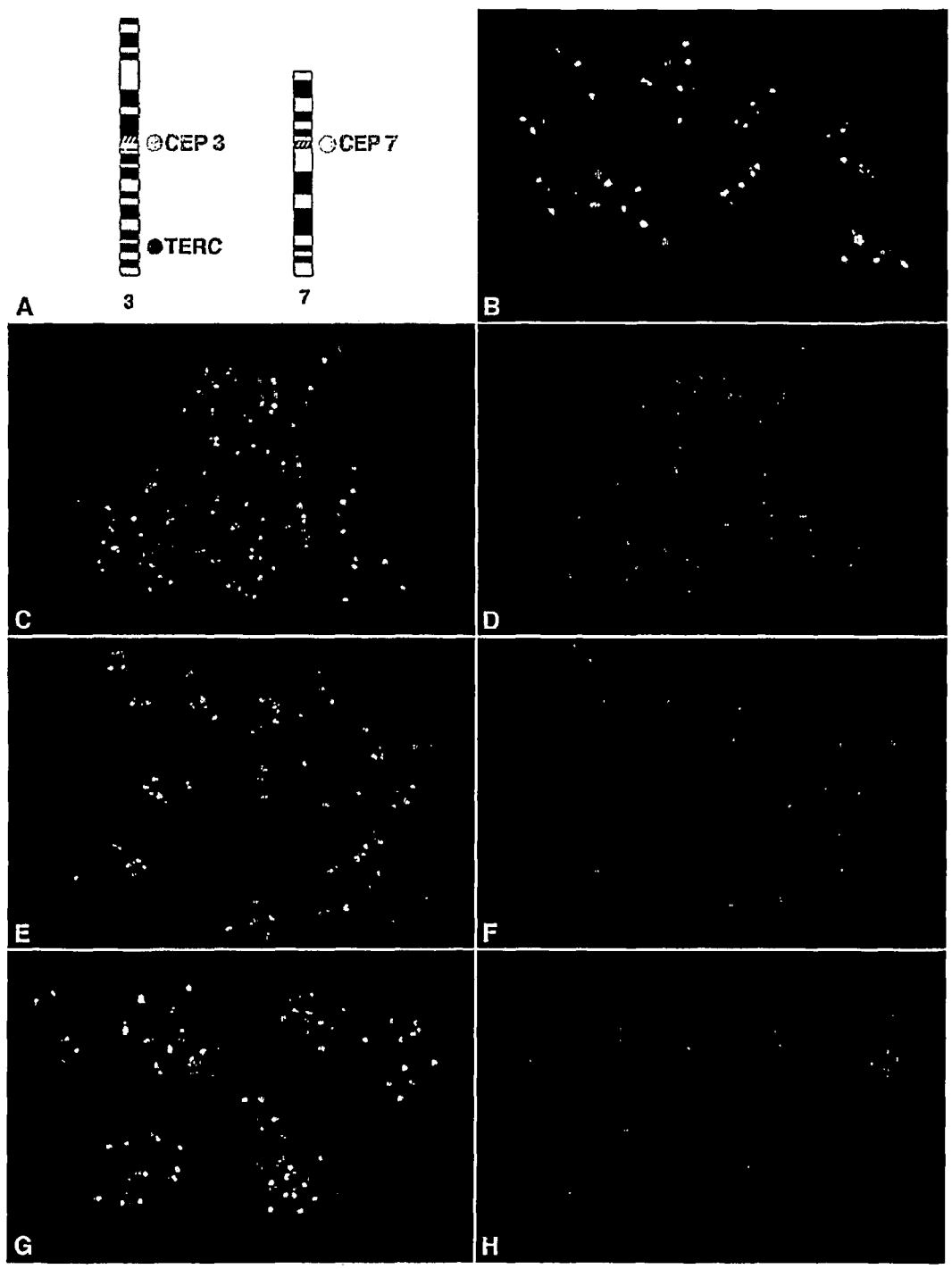
FIG. 4 depicts interphase FISH analysis of showing gain of TERC in 3q26 in HPV infected and HPV negative cervical adenocarcinomas. (A) Chromosomal location of the triple colour probe set: CEP 7 (labeled with Spectrum Aqua, which is pseudocoloured in light-blue in panels B, C, E, and G), CEP 3 (Spectrum Green, pseudocoloured in green in panels B, C, E, and G), and TERC (Spectrum Orange, pseudocoloured in red). (B) Normal nuclei with the expected pattern of two signals per probe per nucleus (2-2-2). (C and D) HPV negative case number 4. (E and F) HPV infected case number 6, and (G and H) HPV positive case number 10. All cases exhibit varying extents of gain of TERC. The cell clusters in C, E and G and in D, F and H show cells with identical aberrant signal numbers with either the triple color probe set shown, or with the TERC probe only, respectively.

Twelve cervical adenocarcinomas (Table 6) were evaluated for copy number changes of the TERC locus at chromosomal band 3q26 using interphase FISH. The three-colour probe panel consisting of CEP7-CEP3-TERC was simultaneously hybridized to cytospin slides with interphase nuclei prepared from formalin fixed tissue sections. All cases were successfully hybridized and analyzed, whereby 208 to 641 nuclei per case were scored. FIG. 1 shows representative hybridizations. Both, normal "diploid" patterns (2-2-2), as well as nuclei with non-diploid patterns were observed. The results are summarized in Table 7. In all 12 tumours a significant proportion of "non-diploid" nuclei was detected, and nine of the tumours exhibited >50% "non-diploid" nuclei. In the individual tumours, nuclei with >2 TERC signals were found in similar frequencies as cells with "non-diploid" pattern, and almost all nuclei with "non-diploid" pattern exhibited >2 TERC signals. In the "non-diploid" nuclei a "tetraploid" pattern (4-4-4) was not commonly observed. In ten of the tumors less than 1% of the nuclei exhibited (4-4-4) and in two cases (4-4-4) was seen in 4% and 12% respectively (Table 7). Thus, gain of TERC was present in all tumours studied and was not an effect of "tetraploid" status.

varying proportions of different but recurrent "non-diploid" patterns. Comparison of signal numbers recorded for TERC versus CEP7 and CEP3 showed increased relative TERC copies in the 12 cases studied (range 1.04-2.0; Table 7). The absolute mean number of TERC signals per nuclei ranged between 2.3 (case 11) and 5.2 (case 10), and in five of the tumours nuclei with more than 10 signals were repeatedly encountered (Table 7). FIG. 4 illustrates nuclei of case 10 with amplification of more than 20 TERC signals, together with 6 signals for CEP3 and CEP7 (FIGS. 1G and H). On the level of individual nuclei the distribution of FISH signals for TERC was of similar type, in that the signals were randomly distributed in the nuclei without obvious clustering. These findings demonstrate that the gain of TERC is not only and always a result of increased chromosome 3 copy numbers, but instead a subchromosomal gain/amplification of the TERC gene locus.

Gain of TERC is Independent of HPV Infection Status

The clinical and follow-up information as well as HPV status of the 12 cervical adenocarcinomas are provided in Table 6. Eight cases were HPV positive and four were HPV negative. Very high proportions of "non-diploid" nuclei with >2 TERC signals were demonstrated in HPV positive (83-99%) as well as HPV negative (86-99%) tumours. The absolute numbers of TERC signals per nucleus were similarly increased in HPV positive (mean 3.4; range 2-22) and HPV negative (mean 3.3; range 2-12) tumours. No apparent associations between TERC copy numbers and clinical characteristics, such as age at diagnosis, stage, differentiation, lymph node involvement or outcome at follow-up, were noted. Thus, gain of TERC is characteristic of cervical adenocarcinomas per se, and independent of HPV infection status.

A series of 12 primary cervical adenocarcinomas were analyzed for gain or amplification of the human telomerase gene TERC, which maps to chromosome band 3q26. Eight of

TABLE 7

Results from interphase FISH analysis of the 12 cervical adenocarcinomas.

| Case no | Nuclei counted | "Diploid" [2-2-2] | "Non-diploid"* | "Tetraploid" [4-4-4] | Nuclei with >2 TERC | "Non-diploid" with >2 TERC | Signals per cell: mean (range) | | | Relative TERC vs. | | Most common "non"-diploid" patterns |
|---|---|---|---|---|---|---|---|---|---|---|---|---|
| | | | | | | | CEP7 | CEP3 | TERC | CEP7 | CEP3 | |
| 1 | 376 | 33% | 67% | 1% | 66% | 99% | 2.2 (2-5) | 2.2 (2-5) | 3.0 (2-8) | 1.4 | 1.4 | [2-2-3] [2-2-4] |
| 2 | 391 | 31% | 69% | 0% | 64% | 92% | 2.1 (2-4) | 2.1 (2-4) | 3.2 (2-7) | 1.5 | 1.6 | [2-2-4] [2-2-3] [2-2-5] |
| 3 | 215 | 27% | 73% | 12% | 68% | 94% | 3.0 (2-6) | 3.1 (2-8) | 3.3 (2-9) | 1.1 | 1.1 | [4-4-4] [4-3-4] [4-3-3] [3-3-3] [3-4-4] |
| 4 | 466 | 40% | 60% | 0% | 59% | 99% | 2.0 (1-4) | 3.2 (2-5) | 4.4 (2-12) | 2.1 | 1.4 | [2-4-6] [2-3-5] [2-4-5] [2-4-7] |
| 5 | 336 | 68% | 32% | 1% | 27% | 86% | 2.1 (2-4) | 2.1 (2-4) | 2.4 (2-6) | 1.1 | 1.1 | [2-2-3] [2-2-4] [2-3-2] |
| 6 | 641 | 69% | 31% | 1% | 28% | 92% | 2.0 (0-4) | 2.3 (2-8) | 2.6 (2-8) | 1.3 | 1.1 | [2-3-4] [2-3-5] [2-2-3] [2-3-3] |
| 7 | 412 | 28% | 72% | 0% | 71% | 99% | 2.1 (2-4) | 2.1 (2-8) | 4.2 (2-15) | 2.0 | 2.0 | [2-2-5] [2-2-4] [2-2-6] [2-2-3] |
| 8 | 626 | 46% | 54% | 1% | 54% | 98% | 2.0 (2-4) | 2.2 (2-5) | 2.9 (2-12) | 1.4 | 1.3 | [2-2-4] [2-2-3] [2-3-3] [2-2-5] |
| 9 | 253 | 29% | 71% | 0% | 64% | 91% | 2.6 (2-5) | 3.0 (2-7) | 3.4 (2-11) | 1.3 | 1.1 | [2-2-3] [2-3-3] [2-2-4] [3-2-2] [3-4-4] |
| 10 | 286 | 30% | 70% | 0% | 66% | 95% | 2.7 (2-7) | 2.9 (2-7) | 5.2 (2-22) | 2.0 | 1.8 | [2-2-4] [2-2-3] [2-2-5] [2-2-6] |
| 11 | 393 | 79% | 21% | 4% | 18% | 83% | 2.2 (2-6) | 2.2 (2-6) | 2.3 (2-6) | 1.04 | 1.04 | [2-2-3] [4-4-4] [2-3-2] |
| 12 | 208 | 20% | 80% | 0% | 79% | 99% | 1.9 (0-4) | 2.0 (0-5) | 3.0 (2-7) | 1.6 | 1.5 | [2-2-3] [2-2-4] |

*Background level of deviation from (2-2-2) in normal nuclei is less than 2% (Heselmayer-Hadad et al., 2003)

Intra-Tumour Heterogeneity for Gain and Amplification of the TERC Locus

It was observed that different FISH patterns in the individual cases. For several of the tumors one or a few predominating patterns were seen. In addition all cases exhibited the 12 carcinomas (67%) were HPV-positive (five tumors were positive for HPV 18, two for HPV 16, and one for HPV 45) (Andersson et al, 2003a; Skyldberg et al, 1999). The remaining four tumour specimens were HPV-negative. FISH was then used with a custom designed probe panel that includes the human telomerase gene (TERC) to assess the potential of this genetic marker to ameliorate the morphological diagnosis of cervical adenocarcinomas.

Detection of a trisomy by CGH requires this numerical aberration to be present in at least 40% of the cells. FISH, of course, detects changes on a single cell basis and is therefore not sensitive to dilution. Additionally, small regional low copy number amplicons might escape detection by CGH.

HPV-DNA has not been identified in the same proportion in adenocarcinomas as in squamous cervical carcinomas (Andersson et al, 2003b; Skyldberg et al, 1999; Tenti et al, 1996). Perhaps oncogenic factors other than HPV are more likely to play a role in the malignant transformation of cervical adenocarcinomas (Skyldberg et al, 1999; Pirog et al, 2000).

This data shows that 10 of the 12 women had a normal Pap smear within 3 years prior to the diagnosis of invasive disease, and without wishing to be bound by any particular scientific theory, may support the hypothesis of a rapid-onset carcinoma. On the other hand, since the sensitivity of a Pap smear for the detection of cervical adenocarcinomas is very low (Krane et al, 2001), the rapid-onset hypothesis may not apply to these cases.

Cervical squamous carcinomas are defined by a non-random and recurrent distribution of genomic imbalances. In addition to HPV, the sequential transformation of cervical squamous epithelium requires the acquisition of additional copies of chromosome arm 3q. Using a genomic probe for the TERC gene on chromosome band 3q26 in combination with two centromere specific probes (CEP3 and CEP7), a high copy number of this locus was shown in cervical adenocarcinomas. Gain or amplification of 3q was found in all cervical adenocarcinomas investigated. Application of this probe set provides an objective genetic test for the diagnosis of cervical adenocarcinomas and might assist in the interpretation of smears with a high degree of glandular cells.

An objective molecular marker in this patient group is needed in the art because of the cytomorphologically difficult identification of these cells and the limited numbers of representative cells due to technical problems in sampling these lesions. As shown herein, many women with cervical adenocarcinoma presented with morphologically normal Pap smears, often only 1-2 years prior to diagnosis.

The following specific references, also incorporated by reference, are indicated above by corresponding reference number.

REFERENCES

1. Ghadimi B M, Heselmeyer-Haddad K, Auer G, Ried T: Interphase cytogenetics: at the interface of genetics and morphology. Anal Cell Pathol 1999, 19:3-6
2. Heim S, Mitelman F: Cancer Cytogenetics. New York, Wiley-Liss, 1995
3. Ried T, Heselmeyer-Haddad K, Blegen H, Schrock E, Auer G: Genomic changes defining the genesis, progression, and malignancy potential in solid human tumors: a phenotype/genotype correlation. Genes Chromosomes Cancer 1999, 25:195-204
4. Visakorpi T, Hyytinen E, Koivisto P, Tanner M, Keinanen R, Palmberg C, Palotie A, Tammela T, Isola J, Kallioniemi O P: In vivo amplification of the androgen receptor gene and progression of human prostate cancer. Nat Genet 1995, 9:401-406
5. Dellas A, Torhorst J, Jiang F, Proffitt J, Schultheiss E, Holzgreve W, Sauter G, Mihatsch M J, Moch H: Prognostic value of genomic alterations in invasive cervical squamous cell carcinoma of clinical stage IB detected by comparative genomic hybridization. Cancer Res 1999, 59:3475-3479
6. Ghadimi B M, Grade M, Liersch T, Langer C, Siemer A, Fuzesi L, Becker H: Gain of chromosome 8q23-24 is a predictive marker for lymph node positivity in colorectal cancer. Clin Cancer Res 2003, 9:1808-1814
7. Slamon D J, Leyland-Jones B, Shak S, Fuchs H, Paton V, Bajamonde A, Fleming T, Eiermann W, Wolter J, Pegram M, Baselga J, Norton L: Use of chemotherapy plus a monoclonal antibody against HER2 for metastatic breast cancer that overexpresses HER2. N Engl J Med 2001, 344:783-792
8. Heselmeyer-Haddad K, Janz V, Castle P E, Chaudhri N, White N, Wilber K, Morrison L E, Auer G, Burroughs F H, Sherman M E, Ried T: Detection of genomic amplification of the human telomerase gene (TERC) in cytologic specimens as a genetic test for the diagnosis of cervical dysplasia. Am J Pathol 2003, 163:1405-1416
9. Walboomers J M, Jacobs M V, Manos M M, Bosch F X, Kummer J A, Shah K V, Snijders P J, Peto J, Meijer C J, Munoz N: Human papillomavirus is a necessary cause of invasive cervical cancer worldwide. J Pathol 1999, 189:12-19
10. zur Hausen H: Papillomaviruses and cancer: from basic studies to clinical application. Nat Rev Cancer 2002, 2:342-350
11. Heselmeyer K, Schrock E, du Manoir S, Blegen H, Shah K, Steinbeck R, Auer G, Ried T: Gain of chromosome 3q defines the transition from severe dysplasia to invasive carcinoma of the uterine cervix. Proc Natl Acad Sci USA 1996, 93:479-484.
12. Atkin N B: Cytogenetics of carcinoma of the cervix uteri: a review. Cancer Genet Cytogenet 1997, 95:33-39
13. Freudenberg N, Kortsik C, Ross A: Grundlagen der Zytopathologie. Basel, Karger, 2002, pp 142
14. Solomon D, Davey D, Kurman R, Moriarty A, O'Connor D, Prey M, Raab S, Sherman M, Wilbur D, Wright T, Jr., Young N: The 2001 Bethesda System: terminology for reporting results of cervical cytology. JAMA 2002, 287: 2114-2119
15. Hollander M, Wolfe D: Nonparametric Statistic Methods. New York, John Wiley & Sons Inc., 1999
16. Koss L G: The Papanicolaou test for cervical cancer detection. A triumph and a tragedy. JAMA 1989, 261:737-743
17. Shingleton H M, Patrick R L, Johnston W W, Smith R A: The current status of the Papanicolaou smear. CA Cancer J Clin 1995, 45:305-320
18. Castle P E, Wacholder S, Sherman M E, Lorincz A T, Glass A G, Scott D R, Rush B B, Demuth F, Schiffman M: Absolute risk of a subsequent abnormal pap among oncogenic human papillomavirus DNA-positive, cytologically negative women. Cancer 2002, 95:2145-2151
19. Castle P E, Wacholder S, Lorincz A T, Scott D R, Sherman M E, Glass A G, Rush B B, Schussler J E, Schiffman M: A prospective study of high-grade cervical neoplasia risk among human papillomavirus-infected women. J Natl Cancer Inst 2002, 94:1406-1414
20. Heselmeyer K, Macville M, Schrock E, Blegen H, Hellstrom A C, Shah K, Auer G, Ried T: Advanced-stage cervical carcinomas are defined by a recurrent pattern of chromosomal aberrations revealing high genetic instability and a consistent gain of chromosome arm 3q. Genes Chromosomes Cancer 1997, 19:233-240
21. Kirchhoff M, Rose H, Petersen B L, Maahr J, Gerdes T, Lundsteen C, Bryndorf T, Kryger-Baggesen N, Christensen L, Engelholm S A, Philip J: Comparative genomic hybridization reveals a recurrent pattern of chromosomal aberrations in severe dysplasia/carcinoma in situ of the cervix and in advanced-stage cervical carcinoma. Genes Chromosomes Cancer 1999, 24:144-150

22. Allen D G, White D J, Hutchins A M, Scurry J P, Tabrizi S N, Garland S M, Armes J E: Progressive genetic aberrations detected by comparative genomic hybridization in squamous cell cervical cancer. Br J Cancer 2000, 83:1659-1663

23. Yang Y C, Shyong W Y, Chang M S, Chen Y J, Lin C H, Huang Z D, Wang, Hsu M T, Chen M L: Frequent gain of copy number on the long arm of chromosome 3 in human cervical adenocarcinoma. Cancer Genet Cytogenet 2001, 131:48-53

24. Umayahara K, Numa F, Suchiro Y, Sakata A, Nawata S, Ogata H, Suminami Y, Sakamoto M, Sasaki K, Kato H: Comparative genomic hybridization detects genetic alterations during early stages of cervical cancer progression. Genes Chromosomes Cancer 2002, 33:98-102

25. Hidalgo A, Schewe C, Petersen S, Salcedo M, Gariglio P, Schluns K, Dietel M, Petersen I: Human papilloma virus status and chromosomal imbalances in primary cervical carcinomas and tumour cell lines. Eur J Cancer 2000, 36:542-548

26. Matthews C P, Shera K A, McDougall J K: Genomic changes and HPV type in cervical carcinoma. Proc Soc Exp Biol Med 2000, 223:316-321

27. Hackett J A, Greider C W: Balancing instability: dual roles for telomerase and telomere dysfunction in tumorigenesis. Oncogene 2002, 21:619-626

28. Campion M J, McCance D J, Cuzick J, Singer A: Progressive potential of mild cervical atypia: prospective cytological, colposcopic, and virological study. Lancet 1986, 2:237-240

29. Koss L G, Stewart F, Foote F W, Jordan M J, Bader G M, Day E: Some Histological Aspects of Behavior of Epidermoid Carcinoma in Situ and Related Lesions of the Uterine Cervix. A Long-Term Prospective Study. Cancer 1963, 16:1160-1211

30. Bocking A, Nguyen V Q: Diagnostic and prognostic use of DNA image cytometry in cervical squamous intraepithelial lesions and invasive carcinoma. Cancer 2004, 102: 41-54

31. Matzke M A, Mette M F, Kanno T, Matzke A J: Does the intrinsic instability of aneuploid genomes have a causal role in cancer? Trends Genet 2003, 19:253-256

32. Sudbo J, Kildal W, Risberg B, Koppang H S, Danielsen H E, Reith A: DNA content as a prognostic marker in patients with oral leukoplakia. N Engl J Med 2001, 344:1270-1278

Andersson S, Larson B, Hjerpe A, Silfversward C, Sällström J, Wilander E, Rylander E (2003a) Adenocarcinoma of the uterine cervix: the presence of human papillomavirus and the method of detection. *Acta Obstet Gytzecol Scand* 82: 960-965

Andersson S, Rylander E, Larson B, Sigurdardottir S, Backlund I, Sällström J, Wilander E (2003b) Types of human papillomavirus revealed in cervical adenocarcinomas after DNA sequencing. *Oncol Rep* 10: 175-179

Benedet J L, Bender H, Jones H, 3rd, Ngan H Y, Pecorelli S (2000) FIGO staging classifications and clinical practice guidelines in the management of gynecologic cancers. FIGO Committee on Gynecologic Oncology. *Int J Gynaecol Obstet* 70: 209-262

Bergström R, Sparen P, Adami H O (1999) Trends in cancer of the cervix uteri in Sweden following cytological screening. *Br J Cancer* 81: 159-156

Bittner M L, Morrison L E Legator M S (1996) Direct label transaminated DNA probe compositions for chromosome identification and methods for their manufacture. United States Government Printing Office. Washington D.C. U.S. Pat. No. 5,491,224

Bosch F X, Manos M M, Munoz N, Sherman M, Jansen A M, Peto J, Schiffman M H, Moreno V, Kurman R, Shah K V (1995) Prevalence of human papillomavirus in cervical cancer: a worldwide perspective. International biological study on cervical cancer (IBSCC) study group. *J Natl Cancer Inst* 87: 796-802

Bosch F X, Munoz N (2002) The viral etiology of cervical cancer. *Virus Res* 89: 183-189

Castro J, Heiden T, Wang N, Tribukait B (1993) Preparation of cell nuclei from fresh tissues for high-quality DNA flow cytometry. *Cytometry* 14: 793-804

Dahlgren L, Mellin H, Wangsa D, Heselmeyer-Haddad K, Bjornestal L, Lindholm J, Munck-Wikland E, Auer G, Ried T, Dalianis T (2003) Comparative genomic hybridization analysis of tonsillar cancer reveals a different pattern of genomic imbalances in human papillomavirus-positive and -negative tumors. *Int J Cancer* 107: 244-249

Heselmeyer K, Schrock E, du Manoir S, Blegen H, Shah K, Steinbeck R, Auer G, Ried T (1996) Gain of chromosome 3q defines the transition from severe dysplasia to invasive carcinoma of the uterine cervix. *Proc Natl Acad Sci USA* 93: 479-484

Heselmeyer K, Macville M, Schrock E, Blegen H, Hellstrom A C, Shah K, Auer G, Ried T (1997a) Advanced-stage cervical carcinomas are defined by a recurrent pattern of chromosomal aberrations revealing high genetic instability and a consistent gain of chromosome arm 3q. *Genes Chromosomes Cancer* 19: 233-240

Heselmeyer K, du Manoir S, Blegen H, Friberg B, Svensson C, Schrock E, Veldman T, Shah K, Auer G, Ried T (1997b) A recurrent pattern of chromosomal aberrations and immunophenotypic appearance defines anal squamous cell carcinomas. *Br J Cancer* 76: 1271-1278

Heselmeyer-Haddad K, Janz V, Castle P E, Chaudhri N, White N, Wilber K, Morrison L E, Auer G, Burroughs F H, Sherman M E, Ried T (2003) Detection of genomic amplification of the human telomerase gene (TERC) in cytologic specimens as a genetic test for the diagnosis of cervical dysplasia. *Am J Pathlol* 163: 1405-1416

Heselmeyer-Haddad K, Sommerfeld K, White N M, Chaudhri N, Morrison L E, Palanisamy N, Wang Z Y, Auer G, Steinberg W, Ried T (2005) Genomic amplification of the human telomerase gene (TERC) in pap smears predicts the development of cervical cancer. *Am J Pathol* 166: 1229-1238

Hildesheim A, Hadjimichael O, Schwartz P E, Wheeler C M, Barnes W, Lowell D M, Willett J, Schiffman M (1999) Risk factors for rapid-onset cervical cancer. *Am J Obstet Gynecol* 180: 571-577

Kinney W K, Manos M M, Hurley L B, Ransley J E (1998) Where's the high-grade cervical neoplasia? The importance of minimally abnormal Papanicolaou diagnoses. *Obstet Gynecol* 91: 973-976

Krane J F, Granter S R, Trask C E, Hogan C L, Lee K R (2001) Papanicolaou smear sensitivity for the detection of adenocarcinoma of the cervix: a study of 49 cases. *Cancer* 93: 8-15

Macgregor J E, Campbell M K, Mann E M, Swanson K Y (1994) Screening for cervical intraepithelial neoplasia in north east Scotland shows fall in incidence and mortality from invasive cancer with concomitant rise in preinvasive disease. *BMJ* 308: 1407-1411

Mählck C G, Jonsson H, Lenner P (1994) Pap smear screening and changes in cervical cancer mortality in Sweden. *Int J Gynecol Obstet* 44: 267-272

Parkin D M, Bray F, Ferlay J, Pisani P (2001) Estimating the world cancer burden: Globocan 2000. *Int J Cancer* 94: 153-156

Pirog E C, Kleter B, Olgac S, Bobkiewicz P, Lindeman J, Quint W G, Richart R M, Isacson C (2000) Prevalence of human papillomavirus DNA in different histological subtypes of cervical adenocarcinoma. *Am J Pathol* 157: 1055-1062

Ponten J, Adami H O, Friberg L G, Gustafsson L, Miller A B, Parkin M, Sparen P, Trichopoulos D (1995) HPV and cervical cancer. *Int J Cancer* 63: 317

Sasieni P, Adams J (2001) Changing rates of adenocarcinoma and adenosquamous carcinoma of the cervix in England. *Lancet,* 357: 1490-1493

Sherman M E, Schiffman M H, Lorincz A T, Manos M M, Scott D R, Kuman R J, Kiviat N B, Stoler M, Glass A G, Rush B B (1994) Toward objective quality assurance in cervical cytopathology: correlation of cytopathologic diagnosis with detection of high-risk human papillomavirus types. *Am J Clin Pathol* 102: 182-187

Skyldberg B M, Murray E, Lambkin H, Kelehan P, Auer G U (1999) Adenocarcinoma of the uterine cervix in Ireland and Sweden: human papillomavirus infection and biologic alterations. *Mod Pathol* 12: 675-682

Smith H O, Tiffany M F, Qualls C R, Key C R (2000) The rising incidence of adenocarcinoma relative to squamous cell carcinoma of the uterine cervix in the United States—a 24-year population-based study. *Gynecol Oncol* 78: 97-105

Stoltzfus P, Heselmeyer-Haddad K, Castro J, White N, Silfversward C, Sjövall K, Einhorn N, Tryggvason K, Auer G, Ried T, Nordström B (2005) Gain of chromosome 3q is an early and consistent genetic aberration in carcinomas of the vulva. *Int J Gynecol Cancer* 15: 120-126

Tenti P, Romagnoli S, Silini E, Zappatore R, Spinillo A, Giunta P, Cappellini A, Vesentini N, Zara C, Carnevali L (1996) Human papillomavirus types 16 and 18 infection in infiltrating adenocarcinoma of the cervix: PCR analysis of 138 cases and correlation with histologic type and grade. *Am J Clin Pathol* 106: 52-56

Walboomers J M, Jacobs M V, Manos M M, Bosch F X, Kummer J A, Shah K V, Snijders P J, Peto J, Meijer C J, Munoz N (1999) Human papillomavirus is a necessary cause of invasive cervical cancer worldwide. *J Pathol* 189: 12-19

Vizcaino A P, Moreno V, Bosch F X, Munoz N, Barros-Dios X M, Parkin D M (1998) International trends in the incidence of cervical cancer: I. Adenocarcinoma and adenosquamous cell carcinomas. *Int J Cancer* 75: 536-545

Yang Y C, Shyong W Y, Chang M S, Chen Y J, Lin C H, Huang Z D, Wang, Hsu M T, Chen M L (2001) Frequent gain of copy number on the long arm of chromosome 3 in human cervical adenocarcinoma. *Cancer Genet Cytogenet* 131: 48-53

The invention claimed is:

1. A method for assessing the risk of developing high grade cervical dysplasia or cancer in a patient diagnosed as having low grade cervical dysplasia or no cervical dysplasia, comprising:
   i) obtaining a cervical sample from the patient;
   ii) detecting any genomic amplification of chromosome 3q in the cervical sample; and
   iii) identifying the patient as at risk of developing high grade cervical dysplasia or cancer when genomic amplification of chromosome 3q is detected in the cervical sample; or identifying the patient as not at risk of developing high grade cervical dysplasia or cancer, and/or as having a condition of maintenance or regression of low grade cervical dysplasia, when genomic amplification of chromosome 3q is not detected in the cervical sample.

2. The method of claim 1, wherein the detecting comprises detecting any genomic amplification within the 3q26 locus of chromosome 3q.

3. The method of claim 1, wherein the low grade cervical dysplasia is a cervical intraepithelial neoplasm of grade 1.

4. The method of claim 1, wherein the high grade cervical dysplasia is a cervical intraepithelial neoplasm of grade 2.

5. The method of claim 1, wherein the high grade cervical dysplasia is a cervical intraepithelial neoplasm of grade 3.

6. The method of claim 1, wherein the high grade cervical dysplasia is a carcinoma in situ.

7. The method of claim 2, wherein the genomic amplification is detected by hybridizing the sample to a probe comprising a detectable marker and a nucleic acid sequence that is complementary to a nucleic acid sequence of the 3q26 locus.

8. The method of claim 7, wherein the nucleic acid sequence of the probe is complementary to the telomerase gene, or a portion thereof.

9. The method of claim 7, wherein the detectable marker emits a fluorescent signal.

10. The method of claim 7, wherein the detectable marker is chromogenic.

11. The method of claim 2, wherein the genomic amplification is detected by Polymerase Chain Reaction.

12. The method of claim 2, wherein the detecting of genomic amplification comprises measuring the amount of telomerase polypeptide in the sample.

13. The method of claim 1, wherein the sample is a preparation from a pap smear or a thin layer suspension of cells.

14. The method of claim 1, wherein the patient previously had high grade cervical dysplasia or cancer.

* * * * *